United States Patent
Pitaru

(10) Patent No.: US 10,570,369 B2
(45) Date of Patent: Feb. 25, 2020

(54) PLURIPOTENT AUTOLOGOUS STEM CELLS FROM ORAL MUCOSA AND METHODS OF USE

(71) Applicant: RAMOT AT TEL-AVIV UNIVERSITY LTD., Tel-Aviv (IL)

(72) Inventor: Sandu Pitaru, Ramat Gan (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 183 days.

(21) Appl. No.: 15/360,555

(22) Filed: Nov. 23, 2016

(65) Prior Publication Data

US 2017/0137778 A1    May 18, 2017

Related U.S. Application Data

(63) Continuation of application No. 12/605,781, filed on Oct. 26, 2009, now Pat. No. 9,534,201, which is a continuation-in-part of application No. PCT/IL2008/000518, filed on Apr. 16, 2008.

(60) Provisional application No. 60/915,538, filed on May 2, 2007, provisional application No. 60/914,246, filed on Apr. 26, 2007.

(51) Int. Cl.
    *C12N 5/074*    (2010.01)
    *C12N 5/071*    (2010.01)
    *A61K 35/38*    (2015.01)

(52) U.S. Cl.
    CPC ............ *C12N 5/0607* (2013.01); *A61K 35/38* (2013.01); *C12N 5/0632* (2013.01)

(58) Field of Classification Search
    None
    See application file for complete search history.

(56) References Cited

U.S. PATENT DOCUMENTS

| | | | |
|---|---|---|---|
| 3,753,357 A | 8/1973 | Schwartz | |
| 4,199,022 A | 4/1980 | Senkan et al. | |
| 4,559,298 A | 12/1985 | Fahy | |
| 5,612,205 A | 3/1997 | Kay et al. | |
| 5,721,367 A | 2/1998 | Kay et al. | |
| 5,789,215 A | 8/1998 | Berns et al. | |
| 5,830,698 A | 11/1998 | Reff | |
| 5,873,254 A | 2/1999 | Arav | |
| 5,919,449 A | 7/1999 | Dinsmore | |
| 5,968,829 A | 10/1999 | Carpenter | |
| 6,087,168 A | 7/2000 | Levesque | |
| 6,310,195 B1 | 10/2001 | Colucci et al. | |
| 7,015,037 B1 | 3/2006 | Furcht | |
| 7,052,907 B2 | 5/2006 | Shi | |
| 7,078,230 B2 | 7/2006 | Wilkison | |
| 8,491,883 B2 | 7/2013 | Gosiewska | |
| 8,518,390 B2 | 8/2013 | Kramer | |
| 8,658,152 B2 | 2/2014 | Messina | |
| 9,044,431 B2 | 6/2015 | Sanberg | |
| 9,468,656 B2 | 10/2016 | Kakulas | |
| 9,804,151 B2 | 10/2017 | Shroff | |
| 2002/0197240 A1 | 12/2002 | Chiu | |
| 2003/0031651 A1 | 2/2003 | Lee | |
| 2004/0247574 A1 | 12/2004 | Christopherson | |
| 2005/0031600 A1 | 2/2005 | Mickle | |
| 2005/0032207 A1 | 2/2005 | Wobus | |
| 2005/0147597 A1 | 7/2005 | Ueno | |
| 2006/0211109 A1 | 9/2006 | Totey | |
| 2006/0252151 A1 | 11/2006 | Sramek | |
| 2007/0031384 A1 | 2/2007 | Alala | |
| 2007/0048381 A1 | 3/2007 | Hart | |

FOREIGN PATENT DOCUMENTS

| | | |
|---|---|---|
| EP | 1760144 A2 | 3/2007 |
| WO | 9732025 A1 | 9/1997 |
| WO | 9903973 A1 | 1/1999 |
| WO | 9919469 A1 | 4/1999 |
| WO | 0003002 A2 | 1/2000 |
| WO | 0015764 A2 | 3/2000 |
| WO | 03089631 A1 | 10/2003 |
| WO | 2004009758 A2 | 1/2004 |
| WO | 2004065589 A1 | 8/2004 |
| WO | 2006017567 A2 | 2/2006 |
| WO | 2007020611 A2 | 2/2007 |

OTHER PUBLICATIONS

Ross et al. Physical Therapy 96(5) 733-742. 2016.*
Dasari et al. World J Stem Cells 6(2) 120-133. 2014.*
Agha-Hosseini, et al., "In vitro isolation of stem cells derived from human dental pulp" Clin Transplant 24: E23-E28 (2010).
Dhanasekaran et al., "A comprehensive study on optimization of proliferation and differentiation potency of bone marrow derived mesenchymal stem cells under prolonged culture condition" Cytotechnology 65:187-197 (2013).
Marappagounder et al., "Long-term culture optimization of human omentum fat-derived mesenchymal stem cells" Cell Biol. Int. 36: 1029-1036 (2012).
Pal et al., "Phenotypic and functional comparison of optimum culture conditions for upscaling of bone marrow-derived mesenchymal stem cells" J Tissue Eng Regen Med, 3:163-174 (2009).
Cobourne et al, "Tooth and Jaw: Molecular Mechanisms of Patterning in the First Branchial Arch" Archives of Oral Biology 48:1-14(2003).
Manrynka-Kalmani et al., "The Lamina Propria of Adult Human Oral Mucosa Harbors a Novel Stem Cell Population" Stem Cells 28:984-995 (2010).
Ulloa-Montoya et al., "Comparative transcriptome analysis of embryonic and adult stem cells with extended and limited differentiation capacity" Genome Biology 8:R163 (2007).
Abranches et al., "Neural Differentiation of Embryonic Stem Cells in vitro: a Road Map to Neurogenesis in the Embryo" PLoS One 4:e6286 (2009).

(Continued)

*Primary Examiner* — Blaine Lankford

(74) *Attorney, Agent, or Firm* — Browdy and Neimark, PLLC

(57) ABSTRACT

The present invention provides a new readily accessible source of adult somatic stem cells from the gastrointestinal tract in general and oral mucosa in particular, methods for isolating pluripotent stem cells from oral mucosa, cells derived therefrom and uses thereof.

27 Claims, 18 Drawing Sheets

(56) References Cited

OTHER PUBLICATIONS

Altaner et al., "Characterization of Mesenchymal Stem Cells of "No-Options" Patients with Critical Limb Ischemia Treated by Autologous Bone Marrow Mononuclear Cells" PLoS One e73722 8(9):1-9 (2013).
Roobrouck et al., "Differentiation Potential of Human Postnatal Mesenchymal Stem Cells, Mesoangioblasts, and Multipotent Adult Progenitor Cells Reflected in Their Transcriptome and Partially Influenced by the Culture Conditions" Stem Cells 29:871-882 (2011).
Brunette et al., "Culture and Origin of Epithelium-Like and Fibrobrast-Like Cells From Porcine Periodontal Ligament Explants and Cell Suspensions" Arch Oral Biol. 21:393-400 (1976).
Liu et al., "A Collagenous Cementum-Derived Attachment Protein Is a Marker for Progenitors of the Mineralized Tissue-Forming Cell Lineage of the Periodontal Ligament" Journal of Bone and Mineral Research 12(10):1691-1699 (1997).
Pitaru et al., "Specific cementum attachment protein enhances selectively the attachment and migration of periodontal cells to root surfaces" J. Periodont Res 30:360-368 (1995).
Pitaru et al., "Bone Morphogenetic Protein 2 Induces the Expression of Cementum Attachment Protein in Human Periodontal Ligament Clones" Connective Tissue Research, 43:2-3, 257-264 (2002).
Sanchez-Ramos, "Neural Cells Derived From Adult Bone Marrow and Umbilical Cord Blood" Journal of Neuroscience Research 69:880-893 (2002).
Widera et al., "Adult Palatum as a Novel Source of Neural Crest-Related Stem Cells" Stem Cells 27:1899-1910 (2009).
Izumi et al., "Development and characterization of a tissue-engineered human oral mucosa equivalent produced in a serum-free culture system" J Dent Res 79(3):798-805 (2000).
Meirelles et al., "Mesenchymal stem cells reside in virtually all post-natal organs and tissues" Journal of Cell Science. 119 2204-2213 (2006).
Bradley et al., "Stem cell medicine encounters the immune system", Nat Rev Immunol 2:859-871, (2002).
Brunstein et al., "Cord blood transplantation for adults", Vox Sanguinis 91:195-205 (2006).
D'Amour et al., "Production of pancreatic hormone-expressing endocrine cells from human embryonic stem cells" Nature Biotechnology 24(11):1392-1401 (2006).
D'Ippolito Get al., "Sustained stromal stem cell self-renewal and osteoblastic differentiation during aging", Rejuvenation Research 9(1):10-19 (2006).
Dabeva and Shafritz, "Activation, proliferation, and differentiation of progenitor cells into hepatocytes in the D-galactosamine model of liver regeneration", Am. J. Pathol. 143, 1606 (1993).
De Coppi et al., "Isolation of amniotic stem cell lines with potential for therapy", Nature Biotechnology 25, 100-106 (2007).
Drukker and Benvenisty, The immunogenicity of human embryonic stem-derived cells, Trends in Biotechnology. 22:136-141 (2004).
Fernandes KJL et al., "A dermal niche for multipotent adult skin-derived precursor cells", Nat Cell Bioi.; 6(11):1082-1093 (2004).
Hallock GG., "In utero cleft lip repair in AIJ mice", Plastic Reconstructive Surgery 75:785-788, (1985).
Ioris AM et al., "Characterization of an amorphous deposit in the lamina propria in oral snuff users in the Sudan as collagen", J Oral Pathol Med; 27(4): 157-162 (1998).
Janzen et al., "Stem-cell aging modified by the cyclin-dependent kinase inhibitor p161NK4a", Nature 28;443 (7110):421-426, (2006).
Laino et al. "An approachable human adult stem cell source for hard-tissue engineering", J. Cell. Physiol. 206, 693-701 (2005).
McDonald et al., Transplanted embryonic stem cells survive, differentiate and promote recovery in injured rat spinal cord, Nat. Med. 5, 1410 (1999).
Rando TA., "Stem cells, aging and the quest for immortality", Nature 441:1080-1086 (2006).
Rao and Madson, "Stem cells and aging: expanding the possibilities", Mech Ageing Dev 122:713-734 (2001).
Reyes Metal., "Purification and ex vivo expansion of postnatal human marrow mesodermal progenitor cells", Blood 96:2615-2625 (2001).
Rui Dong, "Experimental study on the biological properties and the effects in promoting wound repair of oral mucosal stem cells", China Doctor/Master Dissertations Full-text Database (Doctor), Medical and Health Technology; 12: E074-7, Dec. 15, 2006 (2006).
Sethe et al., "Aging of mesenchymal stem cells", Aging Res Rev 5:91-116 (2006).
Steele JC et al., "Lingual striated muscle hamartoma or herniation?", J Oral Pathol Med; 33(8): 454-455 (2004).
Stephens et al., "A comparison of the ability of intra-oral and extra-oral fibroblasts to stimulate extracellular matrix reorganization in a model of wound contraction", J Dent Res. 75(6):1358-1364 (1996).
Stephens P. et al.,"Non-epithelial oral mucosal progenitor cell populations", Oral Dis, 13(1): 1-10 (2007).
Thomson et al., "Embryonic stem cell lines derived from human blastocysts", Science 282:1145-1147 (1998).
Vats et al., "Stem cells", Lancet 366:592-602, (2005).
Watanabe et al., "Cardiomyocyte transplantation in a porcine myocardial infarction model", Cell Transplant. 7, 239-246, (1998).
Zulewski H. et al., "Multipotential nestin-positive stem cells isolated from adult pancreatic islets differentiate ex vivo into pancreatic endocrine, exocrine, and hepatic phenotypes", Diabetes 50:521-533, (2001).
Gray et al., Prospects for the clinical application of neural transplantation with the use of conditionally immortalized neuroepithelial stem cells, The Royal Society, 354:1407-1421 (1999).
Sugaya et al., Potential Use of Stem Cells in Neuroreplacement Therapies for Neurodegenerative Diseases, International Review of Cytology, 228:1-.
Dezawa et al., Specific induction of neuronal cells from bone marrow stromal cells and application for autologous transplantation, The Journal of Clinical Investigation, 113(12):1701-1710 (2004).
Lindvall et al., Stem cell therapy for human neurodegerative disorders—how to make it work, Nature, 542-550 (2004).
Lindvall et al., Stem cell therapy for human brain disorders, Kidney International, 68: 1937-1939 (2005).
Hellmann et al., Increased survival and migration of engrafted mesenchymal marrow stem cells in 6-hydroxydopamine—lesioned rodents, Neuroscience Letters, 395:124-128 (2006).
Cox, "Safety of Autologous Stem Cell Treatment for Traumatic Brain Injury in Children," ClinicalTrials.gov identifier NCT00254722, first posted Nov. 16, 2005, last updated Mar. 1, 2019, downloaded Jun. 24, 2019, from https://clinicaltrials.gov/ct2/show/NCT00254722?term=stem+cells&recrs=dem&cond=Neurologic+Disorder&rank=42.
Burt, "Stem Cell Therapy for Patients With Multiple Sclerosis Failing Alternate Approved Therapy—A Randomized Study," ClinicalTrials.gov Identifier: NCT00273364, first posted Jan. 9, 2006, last updated Apr. 8, 2019, from https://clinicaltrials.gov/ct2/show/NCT00273364?term=stem+cells&recrs=dem&cond=Neurologic+Disorder&rank=99.
Karussis, "Mesenchymal Stem Cells for the Treatment of MS," ClinicalTrials.gov Identifier: NCT00781872, first posted Oct. 29, 2008, last updated Jun. 13, 2019, from https://clinicaltrials.gov/ct2/show/NCT00781872?term=stem+cells&recrs=dem&cond=Neurologic+Disorder&draw=2&rank=145.
Connick, "Mesenchymal Stem Cells in Multiple Sclerosis (MSCIMS) (MSCIMS)," ClinicalTrials.gov Identifier: NCT00395200, first posted Nov. 2, 2006, last updated Oct. 25, 2011, from https://clinicaltrials.gov/ct2/show/NCT00395200?term=stem+cells&recrs=dem&cond=Neurologic+Disorder&draw=2.
Imperial College London, "Autologous Bone Marrow Stem Cells in Ischemic Stroke," ClinicalTrials.gov Identifier: NCT00535197, first posted Sep. 26, 2007, last updated Jul. 8, 2019, from https://clinicaltrials.gov/ct2/show/NCT00535197?term=stem+cells&recrs=dem&cond=Neurologic+Disorder&draw=2&rank=163.

* cited by examiner

Sox2　　　　　　　Nanog　　　　　　　Oct4

Nestin           NeuN           Neuronal-like Cell

PLURIPOTENT AUTOLOGOUS STEM CELLS FROM ORAL MUCOSA AND METHODS OF USE

RELATED APPLICATION DATA

This application is a Continuation of application Ser. No. 12/605,781, filed Oct. 26, 2009, now U.S. Pat. No. 9,534,201, which is a Continuation-In-Part (CIP) application to International Application No. PCT/IL2008/000518 filed on Apr. 16, 2008, which is based on and claims the benefit of U.S. Provisional Application Nos. 60/915,538 filed on May 2, 2007 and 60/914,246 filed on Apr. 26, 2007, the content of each of which is expressly incorporated herein in its entirety by reference thereto.

FIELD OF THE INVENTION

The present invention is in the field of stem cells. In particular the present invention provides an accessible source of adult somatic stem cells, methods for isolating stem cells from these sources, cells derived therefrom and uses thereof.

BACKGROUND OF THE INVENTION

Regenerative medicine is aimed to regenerate the architecture and function of tissues and organs totally or partially lost due to disease, trauma and ageing (Vats et al., Lancet 366:562-602, 2005). Stem cells are considered crucial building blocks for any regenerative strategy. The challenge and motivation are to find the ways for recruiting and/or delivering to the injured site pluripotent stem cells populations capable of regenerating nonfunctional or lost tissues and organs. The restricted location of tissues resident stem cells and the relative low number of circulating stem cells pose serious doubts whether in vivo recruitment of endogenous stem cells may be a realistic clinical prospect.

There are currently three possible strategies for regenerative stem cell-based therapies: a) stimulation of resident stem cells of the affected tissue. Resident stem cells (SC) have been identified in numerous tissues including in those that are most frequently affected by disease as cardiac, neural, pancreatic, and kidney tissues; b) recruitment of circulating bone marrow-derived multipotent stem cells to the site of damage. These have been identified and found to increase in number following acute damage; c) transplantation of ex-vivo expanded stem cells. In this respect, the challenge is to generate a pluripotent population of stem cells that can be expanded ex-vivo without losing its potency and can be safely transplanted with no adverse reactions.

Three major optional sources for stem cells are currently being investigated i) Embryonic stem cells (ECS); ii) Fetal stem cells (FSC); and iii) Adult (somatic) stem cells (ASC) either autologous or allogeneic.

ESC lines are pluripotent and virtually immortal (Thomson et al., Science 282:1145-1147, 1998), but are still far from clinical applications because of their tendency to undergo transformation when implanted in vivo, their antigenicity (Bradley et al., Nat Rev Immunol 2:859-871, 2002; Drucker et al., Trends in Biotechnology. 22:136-141, 2004), the requirement for a mouse feeder layer for their maintenance and expansion and ethical issues.

Theoretically, FSC could be ideal for therapy as on the one hand they might be sufficiently differentiated not to undergo transformation following implantation and on the other hand they still retain sufficient pluripotent properties. Because of ethical reasons only FSC derived from the umbilical cord are currently utilized. However, similarly to allogeneic ASC, umbilical FSC are considered allogeneic transplantations and therefore their use requires antigenic matching, immunosuppressive therapy and can result in rejection or graft versus host disease (Brunstein et al., Vox Sanguinis 91:195-205, 2006).

Thus, an autologous pluripotent stem cells population derived from the adult is considered the ideal population for tissue and organ regeneration. Bone marrow and to very limited extent, peripheral blood, adipose tissue, skin and muscle are the major sources for autologous adult stem cells. A serious drawback of these sources is that aging and disease substantially lower the functionality and possibly the availability of adult stem cells in the bone marrow and other tissues (Janzen et al., Nature 28; 443(7110):421-26, 2006; Rando T A. Nature 441:1080-1086, 2006; Sethe et al., Aging Res Rev 5:91-116, 2006. Rao and Mattson, 122:713-734, 2001). Another considerable drawback of bone marrow-derived pluripotent stem cells is their rarity and cumbersome isolation procedures (Reyes M et al., Blood 96:2615-2625, 2001; D'Ippolito G et al., Rejuvenation Research 9:10-18, 2006).

Aging and associated diseases decrease tissue response to stress. This has been in part attributed to reduction in the tissue specific stem cells functionality as reflected by reduced self-renewal, homing and engraftment abilities (Janzen et al., Nature 28; 443(7110):421-26, 2006). Although the reasons for these changes are still debated, they are considered inherent to aging and/or imposed by epigenetic factors such as changes in stem cells niche.

US 2005/0032207 discloses a method for isolating, culturing and differentiating intestinal stem cells for therapeutic uses. According to this application undifferentiated somatic intestinal stem cells are isolated from intestinal epithelium of a tissue which can comprise portion of the: stomach, duodenum, jejunum, ileum, cecum, colon, e.g. ascending colon, transverse colon, descending colon, sigmoid colon, rectum, anal canal, and/or appendix.

Oral Mucosa

Oral Mucosa is the mucosal lining the oral cavity (FIG. 1). It is a complex tissue consisting of cell populations and the extracellular matrix which houses the cells and provides a substrate for cell attachment. Oral mucosa consists of an epithelial tissue of ectodermal origin and the lamina propria which is a connective tissue of ectomesenchymal origin (FIG. 2). The epithelial part comes into contact with the oral cavity and functions as a barrier that is continuously renewed by a unipotent stem cell population located on the basement membrane, a structure which connects the epithelial and ectomesenchymal parts together. The lamina propria supports the epithelial tissue and is attached to the underlying structures of the oral cavity which are protected by the oral mucosa. Clinical observations indicate that full thickness incisional and excisional surgical wounds in the oral mucosa heal substantially faster than wounds in other connective tissues (Cate R A. Repair and Regeneration of Oral Tissues in Ten Cate's Oral Histology sixth edition 2003; Stephens et al., J Dent Res. 75(6):1358-1364, 1996) and that similarly to early fetal mammalian tissues and a number of adult tissues in low vertebrates, wounds in the oral mucosa heal by regeneration and not by scar formation (Hallock G G., Plastic Reconstructive Surgery 75:785-788, 1985).

It has been disclosed that stem cells suitable for use in therapy may be obtained from various sources. Laino et al. (J. Cell. Physiol. 206, 693-701, 2005) discloses an approachable human adult stem cell source derived from dental pulp (i.e., the cell mass within the tooth), particularly suitable for hard-tissue engineering. U.S. Pat. No. 7,052,907 discloses and claims a culture of isolated human dental pulp stem cells. US Patent Application Publication No. 2006/0252151 discloses methods for harvesting stem cells from dental pulp.

U.S. Pat. No. 7,015,037 discloses the isolation of multipotent adult progenitor cells derived from bone marrow, characterization and uses thereof. In particular the multipotent adult progenitor cells co-express CD 49c and CD 90 and have a doubling time of about 36 hours.

U.S. Pat. No. 7,078,230 discloses pluripotent stem cells generated from adipose tissue-derived stromal cells and uses thereof. In particular, the invention includes isolated adipose tissue derived stromal cells that have been induced to express at least one phenotypic characteristic of a neuronal, astroglial, hematopoietic progenitor, or hepatic cells.

PCT publication WO 2004/009758 discloses a method for isolating embryonic-like stem cells from adult sources using the germ stem cell markers expressed in primordial stem cells but not in differentiated somatic cell types.

PCT publication WO 2003/089631 discloses a method for propagating stem cells and/or progenitor cells which may be used with isolated adult human tissue optionally obtainable from the olfactory lamina propria. PCT publication WO 2007/020611 discloses adult human neural stem cells from the olfactory lamina propria.

Thus, there is still an unmet need in the art to identify a readily accessible source of stem cells in mammals, capable of generating an autologous pluripotent population of stem cells that can be expanded in vitro without losing its pluripotency and can be safely retransplanted into the affected donor to achieve tissue and organ regeneration effectively.

SUMMARY OF THE INVENTION

The present invention provides stem cells derived from a readily accessible source, namely the lamina propria of the gastrointestinal tract in general, that of the upper part of the gastrointestinal (GI) tract in particular, and specifically the lamina propria of the oral mucosa and of the gingival oral mucosa. The present invention thus provides methods for obtaining mucosal stem cells, isolated stem cells derived from this source, cultures of mucosal derived stem cells, methods for maintaining or expanding these stem cells, and therapeutic uses thereof.

According to the present invention it is disclosed that the lamina propria of the gastrointestinal tract in general and that of the oral mucosa in particular contains stem cells that can be readily obtained, maintained in culture and used in therapeutic applications.

It is now disclosed that homogenous cell populations exhibiting a multipotent stem cell (MSC) immunophenotype can be generated from multiple donors on a reproducible basis by utilizing a simple culturing method and without making use of any cumbersome techniques for SC sorting and isolation.

According to one aspect of the present invention, stem cells isolated from the lamina propria (LP) of mucosa obtained from the gastrointestinal tract are disclosed.

According to some embodiments the isolated stem cells are derived from the upper part of the gastrointestinal tract.

According to some embodiments the isolated stem cells are derived from an area selected from the group consisting of: oral cavity, pharynx, esophagus, stomach and duodenum.

According to some embodiments, the stem cells are derived from a readily accessible region of the upper part of the gastrointestinal tract selected from the group consisting of the oral cavity, the pharynx and the esophagus.

According to certain embodiments the stem cells are derived from the oral mucosa.

According to some embodiments the stem cells are derived from the gingival oral mucosa.

According to certain specific embodiments the stem cells are from the lamina propria of the oral mucosa and are herein denoted human oral mucosa-derived stem cells (hOMSC).

According to additional embodiments the stem cells are derived from the lamina propria of gingival oral mucosa and are herein denoted human gingival-derived stem cells (hGSC).

According to other embodiments the stem cells are pluripotent, namely capable of generating the three embryonic germ layers and the cell lineages, tissues and organs originating from these layers. According to one embodiment, the stem cells are multipotent, namely capable of forming multiple cell lineages generally derived from one embryonic germ layer. According to a specific embodiment the stem cells are autologous.

According to some embodiments the mucosa-derived stem cells are characterized by expressing at least one pluripotent embryonic stem cell marker selected from the group consisting of: Oct-4, Tra-1-61, Tra1-81, Tra-2-49, Tra-2-54, SSEA1-4, Rex1, Nanog, Sox2 ABCG2, hTert, and Bmi1.

According to yet other embodiments the mucosa-derived stem cells are characterized by expressing at least one pluripotent embryonic stem cell marker selected from the group consisting of: Oct-4, Tra-2-49, Tra-2-54, SSEA1-4, Rex1, Nanog, Sox2 ABCG2, hTert, and Bmi1.

According to additional embodiments the mucosa-derived stem cells are characterized by expressing a plurality of pluripotent embryonic stem cell markers selected from the group consisting of: Oct-4, Tra-1-61, Tra1-81, Tra-2-49, Tra-2-54, SSEA1-4, Rex1, Nanog, Sox2 ABCG2, hTert, and Bmi1.

According to yet other embodiments the mucosa-derived stem cells are characterized by expressing a plurality of pluripotent embryonic stem cell markers selected from the group consisting of: Oct-4, Tra-2-49, Tra-2-54, SSEA1-4, Rex1, Nanog, Sox2 ABCG2, hTert, and Bmi1.

According to certain embodiments the mucosa-derived stem cells are characterized by expressing at least one multipotent mesenchymal stem cell marker selected from the group consisting of: CD29, CD44, CD73, CD90, CD105, CD106, CD117, CD146, CD166 and Stro1+.

According to additional embodiments the mucosa-derived stem cells are characterized by expressing at least one multipotent mesenchymal stem cell marker selected from the group consisting of: CD29, CD44, CD73, CD90, CD105, CD106, CD146, CD166 and Stro1+.

According to some embodiments the mucosa-derived stem cells are characterized by expressing a plurality of the multipotent mesenchymal stem cell markers CD29, CD44, CD 73, CD90, CD117, CD105, CD106, CD146, CD166 and Stro1+.

According to yet other embodiments the mucosa-derived stem cells are characterized by expressing a plurality of the multipotent mesenchymal stem cell markers CD29, CD44, CD 73, CD90, CD105, CD106, CD146, CD166 and Stro1+.

The present invention also provides a population of oral mucosa-derived cells wherein, according to certain embodiments at least 80% of the cells express at least one cell marker selected from the group consisting of Oct-4, Tra-1-

61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117, CD146, CD166 and Strol+.

The present invention also provides a population of oral mucosa-derived cells wherein, according to certain embodiments 15-80% of the cells express at least one cell marker selected from the group consisting of Oct-4, Tra-2-49. Tra-2-54, SSEA1-4, Rex1, Nanog, Sox2 ABCG2, hTert, Bmi1, CD29, CD44, CD 73, CD90, CD105, CD106, CD146, CD166 and Strol+.

According to other embodiments 1-60% of the cells express at least one pluripotent marker selected from the group consisting of: Oct-4, Tra-2-49, Tra-2-54, SSEA1-4, Rex1, Nanog, Sox2 ABCG2, hTert, and Bmi1.

According to yet other embodiments, 80-100% of the cells express at least one multipotent mesenchymal stem cell marker selected from the group consisting of: CD29, CD73, CD90, CD105, CD166.

According to other embodiments 15-35% of the cells express at least one multipotent mesenchymal stem cell marker selected from the group consisting of: CD106, CD146, and Strol+.

The present invention also provides a population of oral mucosa-derived cells wherein 40-80% of the cells express constitutively at least one neural stem cell or neural cell marker selected from the group consisting of nestin, p75, β-III tubulin, glial fibrillar acidic protein (GFAP), and O4.

According to some embodiments at least 80% of the cells of said population express a plurality of said cell markers.

According to some embodiments the cells are pluripotent.

According to some embodiments the pluripotent stem cells are capable of differentiating into cell lineages of mesodermal origin and transdifferentiate into cell lineages of ectodermal and endodermal origin.

According to one embodiment the cells are multipotent.

According to a specific embodiment the cell population comprises cells which were not selected by means of a sorting procedure.

According to a more specific embodiment the mucosa-derived stem cells are characterized by expressing a plurality of markers characteristic of both pluripotent embryonic and multipotent mesenchymal stem cells.

The present invention provides, in another aspect, a method of isolation of stem cells from oral mucosa.

According to a specific embodiment the method comprises the following steps:
 i. obtaining a cell population derived from an oral mucosa;
 ii. exposing the cells obtained in (i) to at least one probe capable of identifying at least one specific stem cell marker,
 iii. sorting of cells by means of a sorting methodology; and
 iv. isolating the stem cells expressing at least one marker specific for stem cells.

According to certain embodiments the method comprises the following steps:
 i. obtaining a cell population, an explant or a culture derived from the mucosa of the gastrointestinal tract;
 ii. exposing the cells obtained in (i) to at least one probe capable of identifying at least one specific stem cell marker;
 iii. sorting of cells by means of a sorting methodology; and
 iv. isolating the stem cells expressing at least one marker specific for stem cells.

According to some embodiments, cells which do not express specific markers are removed from the cell population following step (ii).

According to one embodiment the cell population of (i) is from a culture or an explant of cells derived from the lamina propria of the gastrointestinal tract and particularly the upper part of the gastrointestinal tract.

According to one embodiment the cell population of (i) is from a cell population, culture or an explant of cells derived from oral mucosa.

According to some embodiments the cell population of (i) is derived from the gingival oral mucosa.

According to a specific embodiment the at least one specific gene marker of (ii) is selected from the group consisting of Oct-4, Tra-1-61, Tra1-81, Tra-2-49, Tra-2-54, SSEA1-4, Rex1, Nanog, Sox2 ABCG2, hTert, and Bmi1, CD29, CD44, CD 73, CD90, CD105, CD106, CD117, CD146, CD166 and Strol+.

According to certain embodiments the at least one specific gene marker of (ii) is selected from the group consisting of Oct-4, Tra-2-49. Tra-2-54, SSEA1-4, Rex1, Nanog, Sox2 ABCG2, hTert, and Bmi1, CD29, CD44, CD 73, CD90, CD105, CD106, CD146, CD166 and Strol+.

The stem cell marker of (ii) may be expressed on the cell's surface, e.g. as a surface protein, or within the cell. The term "exposing the cells" encompasses both contacting the cells with probes directed to surface markers and introducing probes into the cells. Introducing into the cells may include genetic probes such as molecular beacons as well as cell surface markers.

According to another embodiment the sorting methodology of (iv) comprises fluorescence activated cell sorting (FACS).

According to another embodiment the probe is labeled with a detectable tracer.

The present invention also provides a culture or an explant comprising expanded stem cells derived from the mucosa of the upper part of the GI tract. According to one embodiment, the stem cells are derived from the lamina propria. According to another embodiment the stem cells are derived from the lamina propria of the oral mucosa. According to yet another embodiment the stem cells are human gingival-derived stem cells (hGSC), namely they are derived from the gingival oral mucosa. Mucosa-derived pluripotent or multipotent stem cells, may be maintained and expanded in tissue culture in an undifferentiated state or in a partially differentiated state. According to various embodiments, these cells can be induced to differentiate into different cell types.

The present invention further provides therapeutic uses of multipotent and pluripotent stem cells derived from mucosa of the upper part of the GI, preferably from the lamina propria, more preferably from the lamina propria of the oral mucosa.

According to one embodiment, the pluripotent or multipotent stem cells isolated are used for gene therapy. Cells are modified by appropriate gene transfer to correct genetic defects or provide genetic capabilities naturally lacking in the stem cells or their progeny. According to one embodiment, the isolated pluripotent stem cells are used for cell therapy. Pluripotent or multipotent stem cells according to the present invention may be administered to the patient in a manner that permits them to graft to the intended tissue site and reconstitute or regenerate the functionally deficient area.

According to some embodiments, gene transfer or non-genetic substances such as proteins and other chemical or physical methods are applied to a cell population, an explant or a culture derived from the mucosa of the gastrointestinal tract and specifically from the lamina propria of the mucosa to produce induced pluripotent stem cells (iPSC).

According to another aspect a method of treating a tissue disorder or deficiency comprising administering to a patient in need thereof a pluripotent or multipotent mucosa-derived stem cell according to the invention, and providing conditions for differentiation of said cells into cells characterizing said tissue, thereby treating the individual suffering from the tissue disorder or deficiency requiring cell or tissue replacement, is disclosed.

According to yet another aspect a method of producing or regenerating a human tissue or organ, comprising administering to a patient in need thereof a pluripotent or multipotent mucosa-derived somatic stem cell according to the invention, is disclosed. The method of treating an individual suffering from a disorder requiring cell or tissue replacement comprises introducing at least one isolated mucosa-derived multipotent or pluripotent stem cell into a tissue of the individual associated with the disorder, thereby treating the individual suffering from the disorder requiring cell or tissue replacement.

According to some embodiments a method of treating an individual suffering from a disorder requiring cell or tissue replacement comprises (a) subjecting at least one pluripotent or multipotent stem cell derived from the lamina propria of the GI, to culturing conditions suitable for inducing cell proliferation, thereby obtaining an expanded stem cell population; (b) subjecting said expanded stem cell population to differentiation protocols and (c) introducing said partly or fully differentiated stem cell population into a tissue of the individual associated with the disorder, thereby treating the individual suffering from the disorder requiring cell or tissue replacement.

According to another embodiment, the method of treating an individual suffering from a disorder or disease requiring cell or tissue replacement comprises:
  (a) subjecting at least one pluripotent or multipotent stem cell derived from the lamina propria of the GI, to culturing conditions suitable for inducing cell proliferation, thereby obtaining an expanded stem cell population; or
  (b) subjecting at least one pluripotent or multipotent stem cell according to claim 1, to culturing conditions suitable for inducing cell differentiation, thereby obtaining differentiated stem cell population; or
  (c) subjecting at least one pluripotent or multipotent stem cell according to claim 1, to culturing conditions suitable for inducing cell proliferation and differentiation, thereby obtaining an expanded and differentiated stem cell population;

and further introducing said expanded, differentiated or expanded and differentiated stem cell population into a tissue of the individual associated with the disorder, thereby treating the individual suffering from the disorder requiring cell or tissue replacement. According to yet another embodiment a method of treating an individual suffering from a disorder requiring cell or tissue replacement comprises (a) subjecting at least one pluripotent or multipotent stem cell derived from the lamina propria of the GI, to culturing conditions suitable for inducing cell proliferation, thereby obtaining an expanded stem cell population; and (b) introducing said expanded stem cell population into a tissue of the individual associated with the disorder, thereby treating the individual suffering from the disorder requiring cell or tissue replacement.

According to various embodiments the disorder or disease is selected from the group consisting of: hematopoietic disease or disorder, neuronal disease or disorder, cartilage or bone disease or disorder, muscular disease or disorder, ligament disease or disorder, heart disease or disorder, vascular disease or disorder, endothelial disease or disorder, liver disease or disorder, pancreatic disease or disorder, gastrointestinal disease or disorder, pulmonary disease or disorder, urogenital disease or disorder, glandular disease or disorder, adrenal disease or disorder, thyroid disease or disorder, skin disease, ophthalmologic disease or disorder. According to specific embodiments the disorder is a genetic disorder.

Essentially all of the uses known or envisioned in the prior art for stem cells can be accomplished with the isolated cells of the present invention derived from the lamina mucosa of the GI or from the lamina propria of the oral mucosa. These uses include diagnostic, prophylactic and therapeutic techniques.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
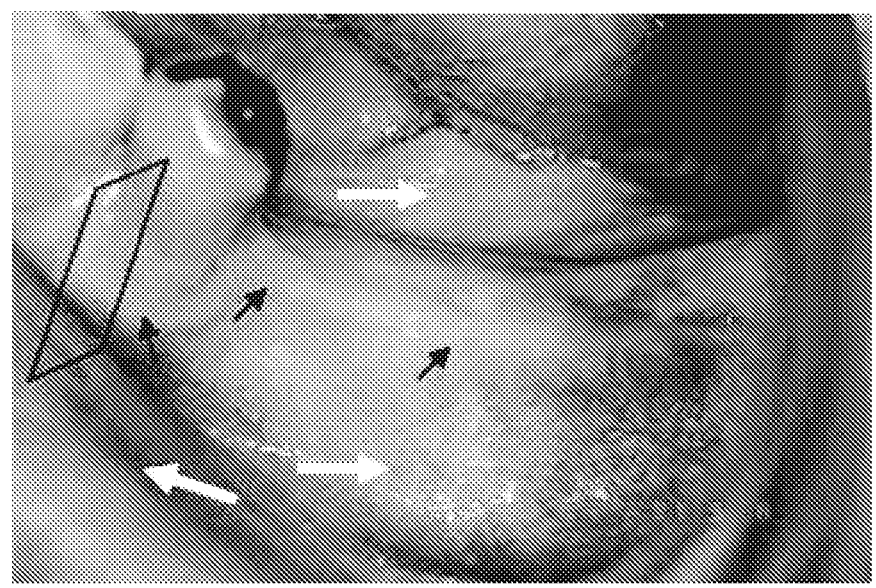
FIG. 1. A clinical illustration of the oral mucosa. Black arrows indicate the gingival tissue which is part of the oral mucosa adjacent to teeth and an edentulous zone. White arrows indicate the lining mucosa which is part of the oral mucosa lining the cheeks, flour of the oral cavity and the oral part of the lips.
Figure 2:
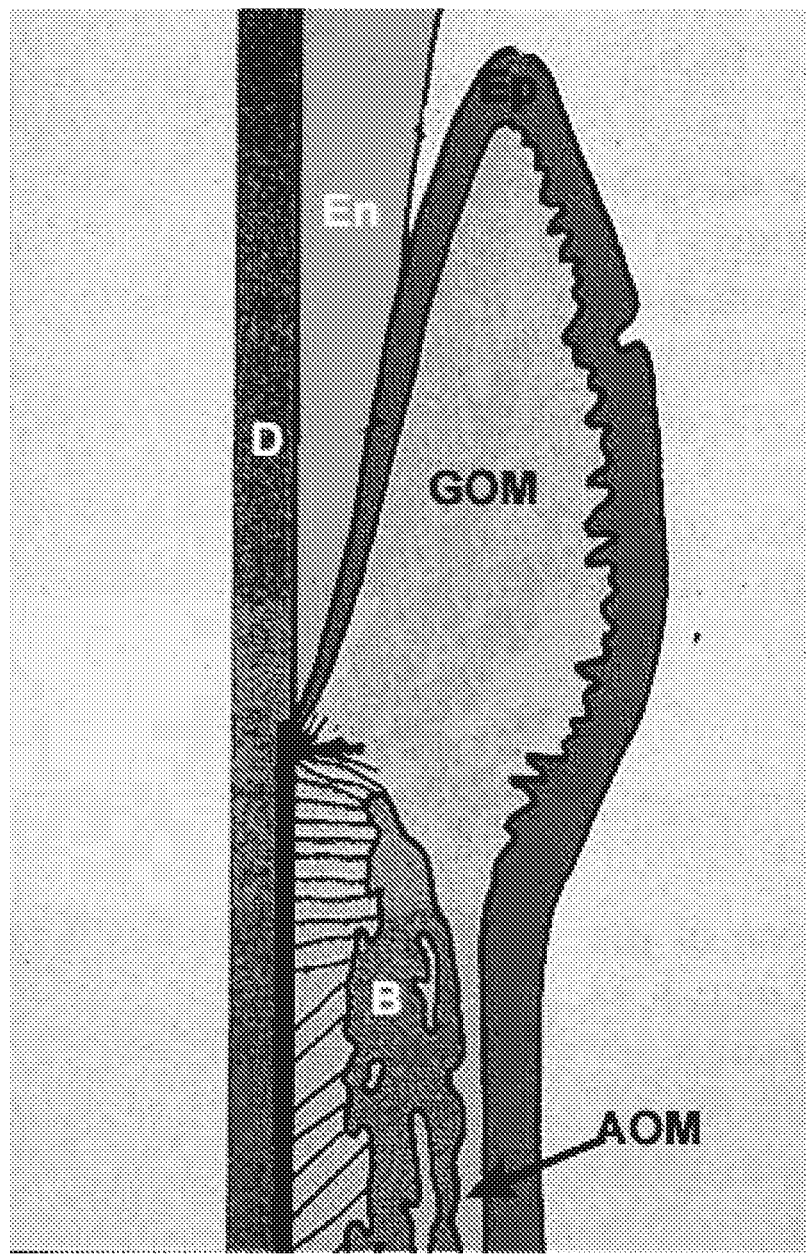
FIG. 2. A schematic histological presentation of a bucco-lingual section performed in the plane shown in FIG. 1. Ep—the epithelium covering the lamina propria of the oral mucosa; GOM—the lamina propria of the gingiva; AOM the lamina propria of the lining mucosa which in this case covers the alveolar bone of the jaw—B; En—the enamel of the tooth; D—the dentine of the tooth.

The novel concept of the present invention, that the easily accessible mucosa lamina propria is enriched with a pluripotent stem cells population the nature of which is not affected by aging or disease, open for the first time the opportunity to obtain a reproducible source for autologous pluripotent stem cells for cell therapy in the adult and elder.

This novel concept is supported by clinical observations indicating that full thickness incisional and excisional surgical wounds in the oral mucosa heal substantially faster than wounds in other connective tissues and that similarly to early fetal mammalian tissues and a number of adult tissues in low vertebrates, wounds in the oral mucosa heal by regeneration and not by scar formation. It is therefore suggested for the first time in the present invention, that the lamina propria contains stem cells capable of responding to wounding and maintaining the homeostasis of this part of the mucosa. Isolation, maintenance and use of these stem cells, as well as of stem cells derived from the oral mucosa of other accessible parts of the upper GI tract, are disclosed in the present invention.

The present invention is based on the unexpected finding that the connective tissue (lamina propria) of the adult oral mucosa is enriched with a fetal-like pluripotent autologous stem cell population, the size and pluripotency or multipotency of which is largely not affected by aging; consequently the oral mucosa is the source of choice for obtaining autologous stem cells with therapeutic potential in the adult and elder.

It is now shown for the first time that whole populations of oral mucosa can be used without requiring laborious purification, as a source for multipotent stem cells capable of differentiating into a variety of cell lineages under in vivo and/or in vitro conditions. This finding is unique to cell populations derived from the lamina propria of the mucosa of the GI tract and particularly to the gingival oral mucosa, and was not observed in other adult tissues.

It is also shown for the first time that the oral mucosa contains a high proportion of pluripotent stem cells as evidenced by their capacity to express markers characteristic to embryonic stem cells. No other adult tissue known in the art was found to contain such a high proportion of pluripotent stem cells. Therefore, the present invention provides oral mucosa as the best source for obtaining pluripotent stem cells from the adult.

The adult lamina propria of the oral mucosa, which can be readily and repeatedly accessed, is a unique adult tissue source for generation of a pluripotent SC population—hOMSC. Regardless of donor age (20-80 years), hundreds of millions of cells, 95% of which express the consensus mesenchymal stem cell (MSC) markers, are simply and reproducibly produced by explanting and expanding a tiny single biopsy in medium supplemented with serum. In contradistinction from MSC of known adult sources more than 40% of hGSC express constitutively typical embryonic SC markers. hGSC differentiate into mesodermal, endodermal and ectodermal lineages and spontaneously express neuronal markers in culture. It is therefore concluded that a distinct SC population is preserved in the adult and elderly lamina propria of the oral mucosa providing a new and superior source for autologous SC therapy.

It should be noted that there are variations between different donors in the expression of stem cell markers.

Gene transfer or non-genetic substances such as proteins and other chemical or physical methods may be applied to a cell population, an explant or a culture derived from the mucosa of the gastrointestinal tract and specifically from the lamina propria of the mucosa to produce induced pluripotent stem cells (iPSC), defined in Takahashi, K. & Yamanaka, S. Cell 2006, 126, 663-676.

A typical isolation method of stem cells from a solid tissue for clinical utilization comprises releasing the cells from the extracellular matrix by enzymatic digestion or by explanation; expanding primary whole population in order to obtain sufficiently large populations; and isolation of stem cells from the whole populations.

Typical whole populations contain low proportion of stem cells and therefore expansion and isolation of stem cells are laborious, long and usually not efficient.

It is herein demonstrated for the first time that primary whole population and expanded whole cell population derived from the lamina propria of the oral mucosa consists mainly (more then 80%) of stem cells. High proportion (80-90%) of cell populations obtained from the oral mucosa of seven different donors are shown herein to express mesenchymal stem cells markers.

The present invention thus provides for the first time a readily available source and a method of use of a stable, pluripotent stem cell population in humans, the size and stemness of which is largely unaffected by aging, and possibly by disease and pharmacological therapy. The isolated stem cells population according to the present invention can be expanded in vitro without loosing its pluripotency and can be safely retransplanted into the affected donor to effectively achieve tissue and organ regeneration.

The finding that adult unsorted whole populations of cells grown in regular culture conditions can transdifferentiate into a cell lineage of a different embryonic origin is unique to the cell populations derived from the oral mucosa and was not observed in culture derived from any adult tissue.

These findings are supported by the finding that whole populations of oral mucosa, differentiated into osteoblastic, chondroblastic and adipocytic lineages can be used "as is" without further purification, as a source for multipotent stem cells (MSC) capable of differentiating into a variety of cell lineages under in vivo and/or in vitro conditions. This finding is unique to cell populations derived from the oral mucosa and was not observed in cultures obtained from any adult tissue. Collectively, the results described in the present application demonstrate that oral mucosa is the best source for obtaining pluripotent stem cells in the adult that are capable of differentiating into cell lineages of mesodermal origin and transdifferentiate into cell lineages of ectodermal and endodermal origin under in vivo and/or in vitro conditions.

Non-limiting examples of mesodermal derived cell lineages are: osteoblastic, adipocytic, chondroblastic, myoblastic, cardiomyoblastic, smooth muscle cells, endothelial cells, hematopoietic, ligamentous, fibroblastic.

Non-limiting examples of cell lineages of ectodermal origin that can be obtained from oral mucosa derived pluripotent stem cells include: neural cells (neurons, astrocytes, ependymal cells, oligodentrocytes and Schwann cells), keratinocytes lining the skin and the oral cavity, glandular epithelium (salivary epithelium, sweat gland epithelium), hair follicle epithelium, corneal epithelium, retinal cells, glandular cells of the adenohypophysis and adrenal medulla, ameloblasts and any other epithelial cell line that is derived from the embryonic ectoderm or neuroectoderm. Examples of tissues and organs that can be treated and/or repaired or regenerated by utilizing pluripotent stem cells derived from the oral mucosa or the herein mentioned ectodermal cell lineages generated from oral mucosa derived stem cells or the combination of these are: epidermis, the epithelial component of the oral mucosa, nervous tissue, cornea, retina and particularly the macula salivary glands, hair, respiratory epithelium and any other tissues or organs derived from the embryonic ectoderm.

Non-limiting examples of cell lineages of endodermal origin include: hepatocytes, cell of the biliary ducts, pancreatic acinar cells. β-islets cells (Langerhans cells), epithelial components of the respiratory tract (e.g. ciliated columnar cells, goblet cells, alveolar epithelium), urinary epithelium including podocytes, gastrointestinal epithelium (e.g. parietal cells, chief cells, various types of glandular gastric and intestinal epithelium, enterocytes), endocrine epithelium of: the adrenal cortex, thyroid and parathyroid and any other cell lineage derived from the embryonic endoderm. Examples of tissues and organs that can be treated and/or repaired or regenerated by utilizing pluripotent stem cells derived from the oral mucosa or the herein mentioned endodermal cell lineages generated from oral mucosa derived stem cells or the combination of these are: hepatic tissue, endocrine pancreas (β-islets), exocrine pancreas, respiratory tracts (e.g. trachea, bronchi) lung pharenchyma, urinary tracts, kidney tissue, thyroid and parathyroid pharenchyma, gastric and intestinal tissue and any other tissues and organs derived from the embryonic endoderm.

Non-limiting examples of tissues and organs that can be treated and/or repaired or regenerated by utilizing whole cell populations derived from the oral mucosa or by utilizing cell lineages at various stages of differentiation generated from the whole populations include: bone, cartilage (hyaline and articular), blood vessels, ligaments, tendons, myocardium, hematopoietic system, muscular tissue, dermis, heart valves, the mesenchymal part of intestinal tubes (e.g. column, esophagus, ileum, rectum), urogenital vessels (e.g. urethra, ureter, urinary bladder), periodontal tissues (e.g. alveolar bone, periodontal ligament, cementum, gingiva), dentin and any other mesenchymal tissue or mesenchymal component of any tissue of the adult or fetal organism.

Non-limiting examples of diseases that can be treated by utilizing whole cell populations or pluripotent stem cells and/or various cell lineages derived from the oral mucosa include: bone fractures in general and vertebral stabilization in particular, osteoporosis, ligament rupture, osteoarthritis, any arthritis of autoimmune origin, traumatic articular cartilage damage, myocardial infarction, heart failure, mitral or aortic valves insufficiency, coronary insufficiency, diabetes, hepatic insufficiency or failure, reflux, fecal incontinence, urinary incontinence, renal insufficiency or failure, emphysema, Parkinson disease, muscular atrophies, muscular dystrophies, amyotrophic lateral sclerosis, multiple sclerosis and other demyelinating diseases, myasthenia gravis, polymyositis, loss of brain tissue caused by cerebrovascular diseases or encephalitis or meningitis, insufficiency and failure of endocrine glands (e.g. hypothyroidism, hypoparathyroidism, pituitary and adrenal hypofunction), acquired or induced failure of the hematopoietic system, periodontal disease and loss of any other tissue(s) mass and function caused by degenerative, inflammatory, proliferative, infectious, malignant diseases, trauma and aging.

According to this invention the whole cell populations or pluripotent stem cells and/or various cell lineages derived from the oral mucosa can be modified by transfection with specific genes that are known in the art to simulate functional and morphological differentiation of these cells into mature tissues and organs. Non-limiting examples of families of such genes include: TGFβ, FGF, PDGF, EGF, hedgehog, Arx, Barx, C-Myb, Catenin, Dlx, Egr, Gli, Hand, Irx, Islet, Lef, Lhx, Msx, N-myc, Pax, Pdx, Pitx, Runx, Snai, Sox, Wt and others gene families known in the art.

According to the present invention, the whole cell populations or pluripotent stem cells and/or various cell lineages derived from the oral mucosa and/or the whole cell populations or pluripotent stem cells and/or various cell lineages derived from the oral mucosa modified by transfection can be delivered to the patient without any carrier or by the means of a carrier. Non-limiting examples of carriers, known in the art, which may be used according to the present invention include:

a. Extracellular matrix components such as collagens, glycoprotein, proteoglycans, glycans as hyaluronic acid fibrin, and others and a combination of these. These type of carriers may take the form of gels or solid structures that may be porous of sizes ranging from nanometers to centimeters.

b. Natural or synthetic apatites such as hydroxyapatite, deproteinized bone particles, frozen dried bone particles, demineralized frozen died bone particle, calcium phosphates as tricalcium phosphate, calcium sulfates, calcium carbonates and other natural and synthetic salts known in the art and combinations of these.

c. Synthetic organic polymers as polylactates, polyfumarates, polyglycolics and others known in the art or their combination.

In an in vivo study it was found that implantation of a suspension of hGSC in the infarcted myocardium of nude rats does not result in teratoma formation as reported for ESC pointing to their safety. Furthermore, these cells migrated from the site of implantation and populated the infarcted myocardium. In a separate study, the implantation of hOMSC subcutaneously, resulted in the formation of bone, cartilage, fat, skeletal muscle, neurons, Schwann cells and epithelial, pointing to the pluripotency of the hOMSC. Thus, the lamina propria of the oral mucosa which can be accessed repeatedly with negligible morbidity is a unique adult source for generating autogenous pluripotent SC populations for therapeutic purposes.

Definitions

"Stem cells" (SC) are undifferentiated cells, which can give rise to a succession of mature functional cells.

"Embryonic stem (ES) cells" are cells derived from the inner cell mass of the embryonic blastocysts that are pluripotent, thus possessing the capability of developing into any organ or tissue type.

"Adult stem cells" are stem cells derived from tissues, organs or blood of an organism, excluding the inner cell mass of the embryo.

"Pluripotent stem cells" are stem cells capable of generating the three embryonic germ layers and the cell lineages, tissues and organs originating from these layers;

"Multipotent stem cells" are stem cells capable of forming multiple cell lineages generally derived from one embryonic germ layer.

"Unipotent stem cells" are stem cells which give rise to a single cell lineage.

"hOMSC" denotes human stem cells derived from the lamina propria of the oral mucosa.

"hGSC" denotes human gingival-derived stem cells.

Differentiated stem cells or stem cell population according to the present invention refer to partially or fully differentiated stem cells or stem cell population.

The upper part of the GI includes the readily accessible regions of the oral cavity, the pharynx, the esophagus, the stomach and the duodenum.

The term "oral mucosa" refers to the mucosal lining the oral cavity, namely: the cheeks and the alveolar ridge including the gingiva and the palate, the floor of the mouth and the oral part of the lips. Oral mucosa according to the present invention encompasses the lamina propria and does not encompass the epithelial part.

ECS refers to Embryonic stem cells, FSC refers to Fetal stem cells; ASC refers to Adult (somatic) stem cells, either autologous or allogeneic; LP refers to lamina propria; OMC refers to oral mucosa-derived cells; MSC refers to multipotent stem cells.

Separation Methods

Separation of the stem cells according to the present invention may be performed according to various physical properties, such as fluorescent properties or other optical properties, magnetic properties, density, electrical properties, etc. Cell types can be isolated by a variety of means including fluorescence activated cell sorting (FACS), protein-conjugated magnetic bead separation, morphologic criteria, specific gene expression patterns (using RT-PCR), or specific antibody staining.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Cells may be selected based on light-scatter properties as well as their expression of various cell surface antigens. The purified stem cells have low side scatter and low to medium forward scatter profiles by FACS analysis.

Various techniques can be employed to separate the cells by initially removing cells of dedicated lineage. Monoclonal antibodies are particularly useful. The antibodies can be attached to a solid support to allow for crude separation. The separation techniques employed should maximize the retention of viability of the fraction to be collected.

The separation techniques employed should maximize the retention of viability of the fraction to be collected. Various techniques of different efficacy may be employed to obtain "relatively crude" separations. Such separations are where up to 30%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

Techniques providing accurate separation include fluorescence activated cell sorters, which can have varying degrees of sophistication, e.g., a plurality of color channels, low angle and obtuse light scattering detecting channels, impedance channels, etc.

Other techniques for positive selection may be employed, which permit accurate separation, such as affinity columns, and the like.

Antibodies used for separation may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

While it is believed that the particular order of separation is not critical to this invention, the order indicated is preferred. Preferably, cells are initially separated by a coarse separation, followed by a fine separation, with positive selection of one or more markers associated with the stem cells and negative selection for markers associated with lineage committed cells.

Use of Stem Cells for Diagnostic and Therapeutic Purposes
Cell Therapy

A significant challenge to the use of stem cells for therapy is to control growth and differentiation into the particular type of tissue required for treatment of each patient. Methods for achieving or promoting this type of use have been disclosed in the art. The following are merely examples of suitable methods for utilizing stem cells in cell therapy.

Organ and Tissue Therapy Applications Using Undifferentiated Cells

US 2002/197240 describes a method of inducing tissue and/or organ repair in vivo without eliciting an immune response. The method includes the transplantation of undifferentiated stem cells into a recipient suffering from tissue and/or organ damage. Undifferentiated cells of the present innovation can be transplanted following isolation to induce tissue and/or to repair organ of a recipient suffering from tissue and/or organ damage.

US 2004/247574 describes methods for improving engraftment efficiency in stem cell transplants by improving stem cell homing to bone marrow. Cells according to the present invention can be used for inducing organ function, tissue reconstitution or regeneration in a human patient in need thereof. The cells are administered in a manner that permits them to graft to the intended tissue site and reconstitute or regenerate the functionally deficient area.

Organ and Tissue Therapy Applications Using Differentiated Cell Cultures

U.S. Pat. No. 6,087,168 is directed to transdifferentiating epidermal cells into viable neurons useful for both cell therapy and gene therapy. Skin cells are transfected with a neurogenic transcription factor, and cultured in a medium containing an antisense oligonucleotide corresponding to a negative regulator of neuronal differentiation.

International Patent Publication WO 97/32025 proposes a method for engrafting drug resistant hematopoietic stem cells. The cells in the graft are augmented by a drug resistance gene (such as methotrexate resistant dihydrofolate reductase), under control of a promoter functional in stem cells. The cells are administered into a mammal, which is then treated with the drug to increase engraftment of transgenic cells relative to nontransgenic cells.

International Patent Publication WO 99/19469 refers to a method for growing pluripotent embryonic stem cells from the pig. A selectable marker gene is inserted into the cells so as to be regulated by a control or promoter sequence in the ES cells, exemplified by the porcine Oct-4 promoter.

International Patent Publication WO 00/15764 refers to propagation and derivation of embryonic stem cells. The cells are cultured in the presence of a compound that selectively inhibits propagation or survival of cells other than ES cells by inhibiting a signaling pathway essential for the differentiated cells to propagate. Exemplary are compounds that inhibit SHP-2, MEK. or the ras/MAPK cascade.

Differentiated cells of the present invention can be used for tissue reconstitution or regeneration in a human patient in need thereof. The cells are administered in a manner that permits them to graft to the intended tissue site and reconstitute or regenerate the functionally deficient area.

Differentiated cells of present invention can also be used for transplant therapy. For example, neural stem cells can be transplanted directly into parenchymal or intrathecal sites of the central nervous system, according to the disease being treated (U.S. Pat. No. 5,968,829). The efficacy of neural cell transplants can be assessed in a rat model for acutely injured spinal cord as described by McDonald et al. (Nat. Med. 5, 1410, 1999).

Forming New Blood Vessels in Damaged Tissue

US 2005/147597 provides methods of forming new blood vessels in diseased or damaged tissue in a subject, methods of increasing blood flow to diseased or damaged tissue in a subject, and methods of increasing angiogenesis in diseased tissue in a subject, which methods comprise: a) isolating autologous bone marrow-mononuclear cells from the subject; and b) transplanting locally into the diseased or damaged tissue an effective amount of the autologous bone-marrow mononuclear cells, thereby forming new blood vessels in the diseased or damaged tissue. Also provided are methods of treating tissue in disease or injury by local transplantation with an effective amount of the autologous bone-marrow mononuclear cells so as to induce vascularization in such diseased tissue.

Cells of the present invention can be used for tissue reconstitution or regeneration in a human patient in need thereof. The cells are transplanted locally in a manner that permits them to graft to the intended tissue site and reconstitute or regenerate new blood vessels in diseased or damaged tissue.

Cell Therapy Applications for Neuronal Disorders

US 2006/211109 describes improved methods for efficiently producing neuroprogenitor cells and differentiated neural cells such as dopaminergic neurons and serotonergic neurons from pluripotent stem cells, for example human embryonic stem cells. The neuroprogenitor cells and terminally differentiated cells of the present invention can be generated in large quantities, and therefore may serve as an excellent source for cell replacement therapy in neurological disorders such as Parkinson's disease.

Certain neural differentiated cells of the present invention may be designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Cell Therapy Applications for Bone/Cartilage Injuries

EP 1760144 describes a cartilage and bone repair composition comprising a group of human mesenchymal stem cells that are differentiated to the chondro-osteogenic lineage, by means of the amplification thereof. The composition can be employed using implants in the area to be repaired or it can be employed directly by injecting the cells in suspension either at the site of the injury or into the systemic circulation for the widespread distribution thereof.

US 2007/048381 describes methods for promoting growth of bone, ligament, or cartilage in a mammal. The methods comprise administering to said mammal a composition comprising a pharmacologically effective amount of a zvegf3 protein in combination with a pharmaceutically acceptable delivery vehicle. Also disclosed are methods for promoting proliferation or differentiation of osteoblasts, osteoclasts, chondrocytes, or bone marrow stem cells.

Cells according to the present invention can be transplanted directly with osteogenic stimulators or transplanted following in-vitro differentiation to chondrogenic, osteogenic, adipogenic and ligamentous cell lineages for tissue regeneration in a human patient in need thereof.

Cell Therapy Applications for Liver Disorders

Hepatocytes and hepatocyte precursors prepared according to the present invention can be assessed in animal models for ability to repair liver damage. One such example is damage caused by intraperitoneal injection of D-galactosamine (Dabeva et al., Am. J. Pathol. 143, 1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cell Therapy Applications for Heart Disorders

WO 2004/065589 and US 2003/031651 describe methods for preparing cells for cell transplantation and transplantation to mammal heart tissue in higher yield, so that it can treat a disorder by unstable heart function.

WO 2006/017567 describes methods of customizing the biological activity (e.g. rhythmic firing rate) of cardiomyocytes derived from pluripotent or multipotent stem cells, followed by transplantation to modify cardiac functions in vivo (e.g. to augment or attenuate the heart rate by modifying the cellular excitability of recipient cells).

US 2005/031600 describes methods and compositions for treating damaged or scarred myocardial tissue, by transplanting mesenchymal stem cells into the damaged or scarred tissue.

Cells of the present invention can be used to treat heart disorders in a human patient in need thereof. Successful treatment will improve heart function as determined by systolic, diastolic, and developed pressure. Cardiac injury can also be modeled using an immobilization coil in the distal portion of the left anterior descending artery (Watanabe et al., Cell Transplant. 7, 239, 1998), and efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

Cell Therapy Applications to Treat Diseases or Disorders of the Pancreas

The pancreas is also a target to be treated or regenerated using pluripotent stem cells derived from the oral mucosa. Pluripotent or multipotent stem cells according to the present invention or endodermal cell lineages generated from oral mucosa derived stem cells, can be used to treat, or prevent diseases, disorders or abnormal states of the endocrine pancreas (β-islets) and the exocrine pancreas.

The disease, disorder or abnormal state is selected, according to one embodiment, from the group consisting of type I or type II diabetes, pancreatitis, pancreatic degeneration and cancers of the pancreas.

US 2007/0031384 disclosed a method of treating diabetes by administering amniotic fluid derived stem cells to a subject. Optionally, the cells may be differentiated into pancreatic-like cells or at least treated to initiate subsequent differentiation into-pancreatic-like cells, prior to administration.

US 2005/0032207 describes use of stem cells differentiated into insulin-producing cells for autologous treatment of diabetes.

Gene Therapy

Gene therapy refers to the transfer and stable insertion of new genetic information into cells for the therapeutic treatment of diseases or disorders. The foreign gene is transferred into a cell that proliferates to spread the new gene throughout the cell population. Thus stem cells, or pluripotent progenitor cells, are usually the target of gene transfer, since they are proliferative cells that produce various progeny lineages which will potentially express the foreign gene.

Pluripotent or multipotent stem cells according to the present invention may be used in gene therapy for the treatment of a variety of diseases, particularly genetic diseases. Genetic diseases associated with hematopoietic cells may be treated by genetic modification of autologous or allogeneic stem cells to correct the genetic defect. For example, diseases including, but not limited to, β-thalassemia, sickle cell anemia, adenosine deaminase deficiency, recombinase deficiency, recombinase regulatory gene deficiency, etc. may be corrected by introduction of a wild-type gene into the selected cells, either by homologous or random recombination. Other indications of gene therapy are introduction of drug resistance genes to enable normal stem cells to have an advantage and be subject to selective pressure during chemotherapy. Diseases other than those associated with hematopoietic cells may also be treated by genetic modification, where the disease is related to the lack of a particular secreted product including, but not limited to, hormones, enzymes, interferons, growth factors, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, one may wish to remove a particular variable region of a T-cell receptor from the T-cell repertoire. By employing homologous recombination, or antisense or ribozyme sequence which prevents expression, the expression of the particular T-cell receptor may be inhibited. For hematotrophic pathogens, such as HIV, HTLV-I and II, etc. the stem cells could be genetically modified to introduce an antisense sequence or ribozyme which would prevents the proliferation of the pathogen in the stem cell or cells differentiated from the stem cells.

Optionally, the progenitor cells obtained using the method of the present invention can be manipulated to express desired gene products. Gene therapy can be used to either modify a cell to replace a gene product, to facilitate regeneration of tissue, to treat disease, or to improve survival of the cells following implantation into a patient (i.e. prevent rejection). In this embodiment, the progenitor cells are transfected prior to expansion and differentiation. Techniques for transfecting cells are known in the art.

A skilled artisan could envision a multitude of genes which would convey beneficial properties to the transfected cell or, more indirectly, to the recipient patient/animal. The added gene may ultimately remain in the recipient cell and all its progeny, or may only remain transiently, depending on the embodiment. For example, genes encoding angiogenic factors could be transfected into progenitor cells isolated from smooth muscle. Such genes would be useful for inducing collateral blood vessel formation as the smooth muscle tissue is regenerated. In some situations, it may be desirable to transfect the cell with more than one gene.

In some instances, it is desirable to have the gene product secreted. In such cases, the gene product preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (Nabel J. G. et al., Thromb Haemost. 70, 202-203, 1993). The desired gene can be transfected into the cell using a variety of techniques. Preferably, the gene is transfected into the cell using an expression vector. Suitable expression vectors include plasmid vectors, viral vectors (such as replication defective retroviral vectors, herpes virus, adenovirus, adenovirus associated virus, and lentivirus), and non-viral vectors (such as for example, liposomes, receptor ligands or electroporation).

The desired gene is usually linked to its own promoter or to a foreign promoter which, in either case, mediates transcription of the gene product. Promoters are chosen based on their ability to drive expression in restricted or in general tissue types, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Cells containing the gene may then be selected for by culturing the cells in the presence of the toxic compound. Methods of targeting genes in mammalian cells are well known to those of skill in the art (U.S. Pat. Nos. 5,830,698; 5,789,215; 5,721,367 and 5,612,205).

The methods of the present invention may be used to isolate and enrich stem cells or progenitors cells that are capable of homologous recombination and, therefore, subject to gene targeting technology. Most studies in gene therapy have focused on the use of hematopoietic stem cells. Recombinant retrovirus vectors have been widely used experimentally to transduce hematopoietic stem and progenitor cells. Genes that have been successfully expressed in mice after transfer by retrovirus vectors include human hypoxanthine phosphoribosyl transferase (Miller, A., et al. Science 255, 630, 1984). Bacterial genes have also been transferred into mammalian cells, in the form of bacterial drug resistance gene transfers in experimental models. The transformation of hematopoietic progenitor cells to drug resistance by eukaryotic virus vectors has been accomplished with recombinant retrovirus-based vector systems (Hock. R. A. and Miller, A. D. Nature 320, 275-277, 1986; Dick, J. E., et al. Cell 42, 71-79, 1985; Eglitis, M., et al., Science 230, 1395-1398, 1985). Adeno-associated virus vectors have been used successfully to transduce mammalian cell lines to neomycin resistance (Tratschin, J. D. et al. Mol. Cell. Biol. 5, 3251, 1985). Other viral vector systems that have been investigated for use in gene transfer include papovaviruses and vaccinia viruses (Cline, M. J. Pharmac. Ther. 29, 69-92, 1985).

Other methods of gene transfer include microinjection, electroporation, liposomes, chromosome transfer, and transfection techniques such as calcium-precipitation transfection technique to transfer a methotrexate-resistant dihydrofolate reductase (DHFR) or the herpes simplex virus thymidine kinase gene, and a human globin gene into murine hematopoietic stem cells. In vivo expression of the DHFR and thymidine kinase genes in stem cell progeny was demonstrated (Salser, W., et al. in Organization and Expression of Globin Genes, Alan R. Liss, Inc., New York, pp. 313-334, 1981).

Gene therapy has also been investigated in murine models with the goal of enzyme replacement therapy. Normal stem cells from a donor mouse have been used to reconstitute the hematopoietic cell system of mice lacking beta-glucuronidase (Yatziv, S. et al. J. Lab. Clin. Med. 90, 792-797, 1982). By this way, a native gene was being supplied and no recombinant stem cells (or gene transfer techniques) were needed.

Cryopreservation

The freezing of cells is ordinarily destructive. On cooling, water within the cell freezes.

Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroys the cell. These injurious effects can be circumvented by (a) use of a cryoprotective agent, (b) control of the freezing rate, and (c) storage at a temperature sufficiently low to minimize degradative reactions.

Considerations and procedures for the manipulation, cryopreservation, and long-term storage of hematopoietic stem cells, particularly from bone marrow or peripheral blood, are known in the art. Some methods were reviewed by Gorin, N. C. in Clinics In Haematology 15, 19-48, 1986. Other methods of cryopreservation of viable cells, or modifications thereof, are available and envisioned for use (e.g., cold metal-mirror techniques; U.S. Pat. Nos. 4,199,022; 3,753,357; 4,559,298). U.S. Pat. No. 6,310,195 discloses a method for preservation of pluripotent progenitor cells, as well as totipotent progenitor cells based on a use of a specific protein. U.S. Pat. No. 5,873,254 discloses device and methods for multigradient directional cooling and warming of biological samples. This method, as well as other methods and devices known in the art for cryopreservation may be used with the cells according to the present invention.

Cryoprotective agents which can be used include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts.

Frozen cells are preferably thawed quickly (e.g., in a water bath maintained at 37-41° C.) and chilled immediately upon thawing. In particular, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In Vitro Cultures of Stem Cells

An optional procedure (either before or after cryopreservation) is to expand the stem in vitro. However, care should be taken to ensure that growth in vitro does not result in the production of differentiated progeny cells at the expense of multipotent stem cells which are therapeutically necessary for reconstitution. Various protocols have been described for the growth in vitro of cord blood or bone marrow cells, and it is envisioned that such procedures, or modifications thereof, may be employed (Dexter, T. M. et al. J. Cell. Physiol. 91, 335, 1977; Witlock, C. A. and Witte, O. N. Proc. Natl. Acad. Sci. U.S.A. 79, 3608-3612, 1982).

WO 2006/085482 describes a technique for amplifying a hematopoietic stem cell ex vivo. By using the amplified hematopoietic stem cell or a stem cell of each of various tissues, a transplantation therapy and a gene therapy for a patient with a variety of intractable hematologic diseases or a variety of organ diseases can be conducted.

Various factors can also be tested for use in stimulation of proliferation in vitro, including but not limited to interleukin-3 (IL-3), granulocyte-macrophage (GM)-colony stimulating factor (CSF), IL-1 (hemopoietin-1), IL-4 (B cell growth factor), IL-6, alone or in combination.

Cells Expansion

The present invention further encompasses methods for obtaining compositions of cells which are highly enriched in stem cells. The method comprises incubating the compositions described above under conditions suitable for generation of stem cells. Compositions comprising the original stem cells and/or the generated stem cells are obtained thereby. Such a composition has utility in reconstituting human hematopoietic systems and in studying various parameters of hematopoietic cells as described above.

The invention also encompasses methods of use of the mucosa-derived stem cells. Since the cells are naive, they can be used to fully reconstitute an immunocompromised host such as an irradiated host or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells becoming committed to a particular lineage, or with their proliferation, maturation and differentiation. The stem cells may also be used in the isolation and evaluation of factors associated with the differentiation and maturation of hematopoietic cells. Thus, stem cells may be used in assays to determine the activity of media, such as conditioned media, evaluate fluids for cell growth activity, involvement with dedication of particular lineages, or the like.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

General Methodologies

Generation of Oral Mucosa Derived-Cells (OMC):

Lamina propria of the attached gingiva and that of the lining mucosa serve as sources for OMC. The rationale for this is that clinical observations and the scientific data point to both types of LP as potential sources for oral mucosa derived stem cell isolation. OMC are generated by culturing gingival or lining mucosa explants or cells released from these explants by successive enzymatic digestions of biopsies as described by McCulloch et al (J Periodont Res 22:41-49, 1986). The culture is performed in low glucose DMEM (LGDMEM) supplemented with 1-20% serum and an antibiotic solution comprising penicillin (100 µg/ml), gentamycin (50 µg/ml) and fungison (0.3 µg/ml). This medium is herein referred "expansion medium". Alternatively, for the generation of MSC cultures are grown in regular DMEM or high glucose DMEM supplemented with 10-20% serum.

Fluorescence-Activated Cell Sorting (FACS):

For staining intracellular molecules cells were fixed in 1.5% paraformaldehyde for 10 minutes, washed 2 times with 0.5 ml cold buffer solution (DPBS, 0.5% BSA, 0.02% sodium azide, pH 7.4), permeabilized with 0.1% Triton X-100 for 10 min, centrifuged, suspended in 100 µl cold buffer solution (DPBS, 0.5% BSA, 0.02% sodium azide, at pH 7.4), stained with the specific conjugated antibody for 30 min, rinsed twice with the cold buffer solution and resuspended with 1 ml PBS. For indirect staining, cells were rinsed once with 1 ml cold buffer solution before staining with a secondary antibody. For cell surface marker staining the Triton X-100 was omitted. Analysis or sorting was done with a FACS scan (BD Bioscience).

Immunofluorescence (IF):

Cell were cultured in 8-wells Labtek chambers. For staining intracellular molecules cells were fixed for 10 min in cold 4% paraformaldehyde, washed 2 times with PBS and permeabilized for 10 min with 0.1% Triton X-100. For cell surface marker staining the Triton X-100 step was omitted. Incubation with the $1^{st}$ and $2^{nd}$ antibodies and blocking was done according to manufactures instructions. Nuclei will be stained with DAPI.

RT-PCR:

Total RNA was extracted using RNA purification kit (Zotal) according to the manufacturer's instructions and quantified spectrophotometrically. Reverse transcription and amplification was done using cDNA synthesis kit (Bio-Rad) with 0.5 µg RNA. For RT-PCR analysis, 1 µl of cDNA was added to 0.5 µM 5' and 3' primers and 25 µl High Fidelity DNA Polymerase (FINNZYME). Amplifications was performed in a GeneAmp 9600 thermocycler (Perkin-Elmer) for 25-30 cycles. Tm was determined using FINNZYME calculation tool after an initial denaturation at 98° C. of 10 seconds. PCR products (10 µl aliquot) were size-separated by electrophoresis in 1.5% agarose gels. The products of the amplification reactions were visualized by electronic autoradiography using a densitometer (Bio-Rad).

Specific Protocols Used for Ectodermal Assessing Differentiation

Neuronal Differentiation:

For neural induction cells of oral mucosa-derived whole populations were plated at low density in 8 wells Labtek plates in DMEM-high glucose (DMEM-HG), 20% FBS with 100 U/ml penicillin and 1 mg/ml streptomycin for 48 hours. Then, commitment was induced by exposing cells to DMEM-HG, 1 mM b-mercaptoethanol (bME), 10 ng/ml NT-3 for 2 days. Differentiation was induced by subjecting the cells to NT-3 (10 ng/ml), NGF (10 ng/ml) and BDNF (50 ng/ml) in DMEM-HG for 10 days.

Specific Protocols Used for Assessing Mesodermal Differentiation

Osteogenic Differentiation:

For osteogenic differentiation cells of oral mucosa-derived whole populations were grown in osteogenic differentiation medium consisting of αMEM supplemented with 15% FCS, $10^{-7}$M dexamathasone, 10 µM β-glycerophosphate and 50 mg/ml vitamin C for 4 weeks.

Chondrogenic Differentiation:

For chondrogenic differentiation cells of oral mucosa-derived whole populations were resuspended in serum-free chondrogenic medium composed of DMEM high-glucose, 100 nM Dex, 10 ng/ml TGF-β3, 50 µg/ml ascorbic acid 2-phosphate. 100 µg/ml sodium pyruvate, 40 µg/ml proline and ITS-plus (final concentrations: 6.25 µg/ml bovine insulin, 6.25 µg/ml transferrin, 6.25 µg/ml selenous acid, 5.33 µg/ml linoleic acid, and 1.25 mg/ml bovine serum albumin; Aliquots of 250,000 cells were suspended in 0.5 ml of chondrogenic medium and distributed between 15-ml conical polypropylene centrifuge tubes (Costar). The cells were centrifuged for 5 minutes at 600 g and left at the bottom of the tube. Tubes were incubated, with caps loosened, in a 100% humidified atmosphere of 95% air. 5% $CO_2$, at 37° C. for up to 4 weeks.

Adipocytic Differentiation:

For adipocytic differentiation oral mucosa-derived whole populations were treated with adipocytic differentiation medium consisting of α-MEM, 10% FBS, 0.5 mM hydrocortisone, 0.5 mM isobutylmethylxanthine, and 60 mM indomethacin for 5 weeks.

Specific Protocols Used for Assessing Endodermal Differentiation

β-Islets Cell Differentiation:

β-islets cell differentiation is induced by plating OMC in DMEM-HG (DMEM-High Glucose), 10-20% serum, for 24 h. Then, the medium is replaced with DMEM-HG+20% serum+10-20 ng/ml bFGF for 24 h. For endodermal specification the medium is replaced by medium consisting of DMEMHG, 1% DMSO, 100 mM butylated hydroxyanisole (BHA), and 10 nM/l exendin-4, for 24-48 hours. Thereafter, endodermal commitment is induced by exposing the cultures to RPMI supplemented with 11.1 mM/l glucose, 10-20% serum, 10 mM/l Hepes, 1.0 mM/l sodium pyruvate. 10-30 ng/ml b-FGF, 10-30 ng/ml EGF and 10 nM/l exendin-4, for 3-6 days. Islet-like differentiation will be induced by exposing the cells to RPMI+2.5 mM/l glucose, 10 mM/l Hepes, 10 mMl/l nicotinamide, 100 pM/l HGF, 10 nM/l exendin-4, and 2.0 nM/l activin-A for 3-15 days. β-islets cells differentiation will be identified by the expression of insulin and glucagon and the transcription factors involved in 3-cell development Beta2/NeuroD, Nkx6.1 and Isl1 at the protein and mRNA levels. Alternative regimens for β-islests differentiation are describe in the art as for example that described in D'Amour et al. (Nature Biotechnologty 24(11): 1392-1401, 2006).

Hepatic Differentiation.

For hepatic differentiation modified protocol from De Coppi et al. (Nature Biotechnology 25, 100-106), is used. Hepatic differentiation is induced by seeding OMC/cm$^2$ on plastic plates coated with Matrigel or laminin and fibronectin and grown to semi-confluent density. The medium is then supplemented with 10-20% serum, 300 mM monothioglycerol, 10-30 ng/ml HGF, 10 ng/ml oncostatin M. $10^{-7}$ M dexamethasone, 100 ng/ml FGF4, 1×ITS (insulin, transferrin, selenium). After 1-3 weeks the cells are harvested and plated between 2 layers of collagen or fibrin gels and maintained in the differentiation medium for additional 30-60 days.

Cell Culture:

Gingival biopsies were obtained from 20 donors following the study approval by the Institutional Helsinki Committee of Sheba Medical Center, Ramat-Gan, Israel. hGSC were generated by explanation as described by us elsewhere (Pitaru, S. et al., 2002, Connect Tissue Res 43, 257-264). Briefly, gingival biopsies 3-4×2×1 mm were minced and explants were cultured in 25 cm$^2$ tissue culture flasks in low glucose DMEM (LG-DMEM) supplemented with 10% FCS and an antibiotic solution comprising penicillin (100 µg/ml), gentamycin (50 µg/ml) and fungison (0.3 µg/ml). This medium is referred herein as expansion medium. For expanding primary cultures ($P_0$), these were grown to 70% confluence, harvested and aliquots of $10^5$ cells were passaged into 25 cm$^2$ tissue cultures flasks and cultured to 50% confluence and passaged repetitively.

Cumulative Doubling Populations:

Cultures obtained from 2 donors were passaged as described above. At each harvesting point the total number of cells in each of 3 separate flasks was counted and the average number of cells was calculated. The number of doublings between two subsequent passages was calculated using the formula (log(10)H−log(10)I)/log(10)2 where H is the harvested cells number and I is the initial plated cells number.

Cloning Efficiency:

Cultures at $P_4$-$P_7$ obtained from 3 young donors and 3 old donors were cloned by limited dilution in 96 well plates in expansion medium (Liu et al., 1997, J Bone Miner Res, 12, 1691-99). Twenty four hours after plating, wells were examined by phase microscopy to exclude wells that comprised more than 1 cell. Fourteen days after cloning cultures were stained with crystal violet to determine the percentage of wells that comprised colonies of more than 50 cells.

Immunophenotyping:

Flow Cytometry Analysis:

Cultures $P_4$-$P_7$ were shortly harvested in trypsin—EDTA. Following trypsin inactivation with 10% FCS, cells were centrifuged and resuspended in blocking buffer (PBS+0.1% BSA and 0.01% sodium azide) and passaged through 70 µm strainer (BD Bioscience, San Jose, Calif. USA) to obtain single cell suspensions. For direct staining of cell surface antigens aliquots of 0.5-1×10$^6$ were transferred to FACS tubes (BD Bioscience, San Jose, Calif. USA), centrifuged, resuspended in 100 µl blocking buffer for 1 hour and stained with conjugated FITC or PE primary antibody according to the manufactures instructions. For indirect staining the cell aliquots were incubated with non-conjugated primary antibodies, centrifuged, washed with 3 ml blocking buffer and incubated with FITC-conjugated secondary antibody according to the manufactures instructions. For intracellular antigens staining single cell suspensions were fixed in 1.5% paraformaldehyde in PBS for 10 minutes, washed in 3 ml of blocking buffer, permeabilized in 0.1% TritonX 100 for 10 min. washed in 3 ml of blocking buffer and then stained as described above. Replacement of the conjugated primary antibodies by their identical conjugated isotype immunoglobulins and omission of the non-conjugated primary antibody served as controls for direct and indirect labeling, respectively. Following antibody labeling cells were centrifuged, washed in blocking buffer, centrifuged, resuspended in Mg and Ca free PBS and analyzed with a FACScan (FACS sorter, BD Bioscience, San Jose, Calif. USA). Win-MDI 2.9 was used to analyze the data. Each marker was analyzed in separate cultures obtained from 3-8 donors from each age group.

Differentiation Regimens:

Osteogenic Differentiation:

hGSC were cultured in osteogenic medium consisting of αMEM supplemented with antibiotics, 12% FCS, 50 µg/ml vitamin C, $10^{-7}$ M dexamethasone (Dex) and 10 µg/ml β-glycerophosphate for up to 5 weeks. The expression of Runx2, osterix, alkaline phosphatase and collagen type I was examined in 1 week old cultures by RT-PCR. Five weeks old cultures were fixed and stained with Alizarin red S as described in Pitaru et al., 1993 (J Bone Miner. Res. 8, 919-29).

Chondrogenic Differentiation:

For chondrogenic differentiation aliquots of 250.000 hGSC were resuspended in serum-free medium in 15-ml conical polypropylene centrifuge tubes, centrifuged to form a micromass and then cultured for 5 weeks in chondrogenic medium composed of DMEM high-glucose, $10^{-7}$ M Dex, 10 ng/ml TGF-β3, 50 µg/ml ascorbic acid, 100 µg/ml sodium pyruvate, 40 µg/ml proline and ITS-plus (final concentrations: 6.25 µg/ml bovine insulin, 6.25 µg/ml transferrin, 6.25 µg/ml selenous acid, 5.33 µg/ml linoleic acid) and 1.25 mg/ml bovine serum albumin. Thereafter, the micromasses were fixed with 4% paraformaldehyde, dehydrated, embedded in paraffin and cut into 6 µm thick sections. For proteoglycans identification sections were stained with 1% alcian blue dissolved in 3% acetic acid and counterstained with nuclear fast red solution. Following rehydration of the sections, CHEMICON IHC Select® Kits (Rosemont, Ill., US) were used according to the manufacturer instruction to identify aggrecan and collagen type II expression.

Adipocytic Differentiation:

To induce adipocytic differentiation hGSC were cultured in medium consisting of αMEM supplemented with antibiotics, 20% FCS, $10^{-6}$ M Dex, 10 µM insulin, 0.5 mM 1-methyl-3-isobutyl-xanthin, and 60 mM indomethacin for 5 weeks. To identify adipocytic differentiation the expression of LPL and PPARγ2 was assessed in 5 weeks old cultures by RT-PCR analysis and the development of adipocytes-like cells comprising triglycerides vacuoles was identified by the Red oil O staining.

Definitive Endoderm Differentiation:

hGSC were plated in Labtek 8 well plates at a concentration of 2500 or 5000 cells/well and maintained in expansion medium supplemented with 100 ng/ml of activin A and 0.5% FCS. The expression of Sox17, FoxA2 and CXCR4 markers were assessed by indirect immunofluorescence in cultures treated with activin A for 48 and 72 hours.

Neuronal Differentiation:

hGSC were plated in Labtek 8 well plates at a concentration of 500 or 1000 cells/well and maintained in expansion medium for 48 hours. Then the medium was replaced with serum free expansion medium supplemented with 10 ng/ml NT3, 10 ng/ml NGF-β, 50 ng/ml BDNF and N2. Cultures were harvested for immunofluorescence 0 (48 hours after plating), 7 and 14 days thereafter. In addition hGSC were plated into 6 well plates at a seeding concentration of $2 \times 10^5$ cells/well and subjected to the same differentiation protocol as above. Cultures were harvested for RT-PCR analysis of Nestin, β-III tubulin, MAP2 and GFAP at 16 days after plating.

Differentiation of Cloned Populations:

Cloned colonies were generated as described above. After 14-21 days the expansion medium was replaced by one of the differentiation media described above. Cultures grown in either osteogenic or adipocytic or chondrogenic media for 21 days were fixed and stained with either Alizarin red S or oil red O or alcian blue, respectively. βIII-tubulin was assessed in cloned cultures grown in neural differentiation medium for 14 days. CXCR4 was assessed in cloned cultures treated for 72 hours with activin A. The experiments were repeated twice for a young and an old donor.

Controls:

In each of the differentiation assays cultures that were maintained only in expansion media served as negative controls.

Statistical Analysis:

t-Test with 2 tails and 2 samples of unequal variance was used to compare the level of marker expression between young- and old-derived hGSC.

Example 1—Clonogenicity Determination

Figure 3:
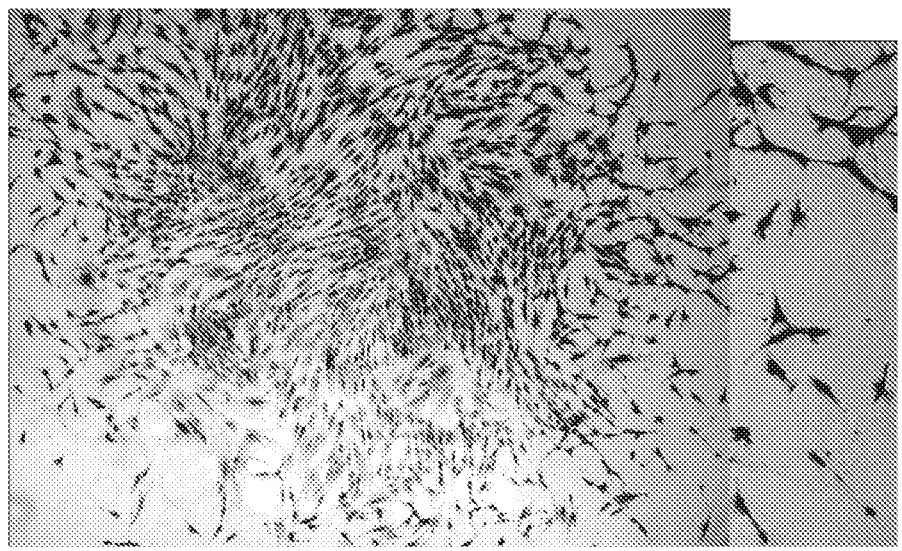
FIG. 3. Left panel: A colony derived from a single cell at 14 days. Right panel: high magnification of the inset shown in the left panel illustrating single cells with a low cytoplasm/nucleus ratio.
Figure 4:
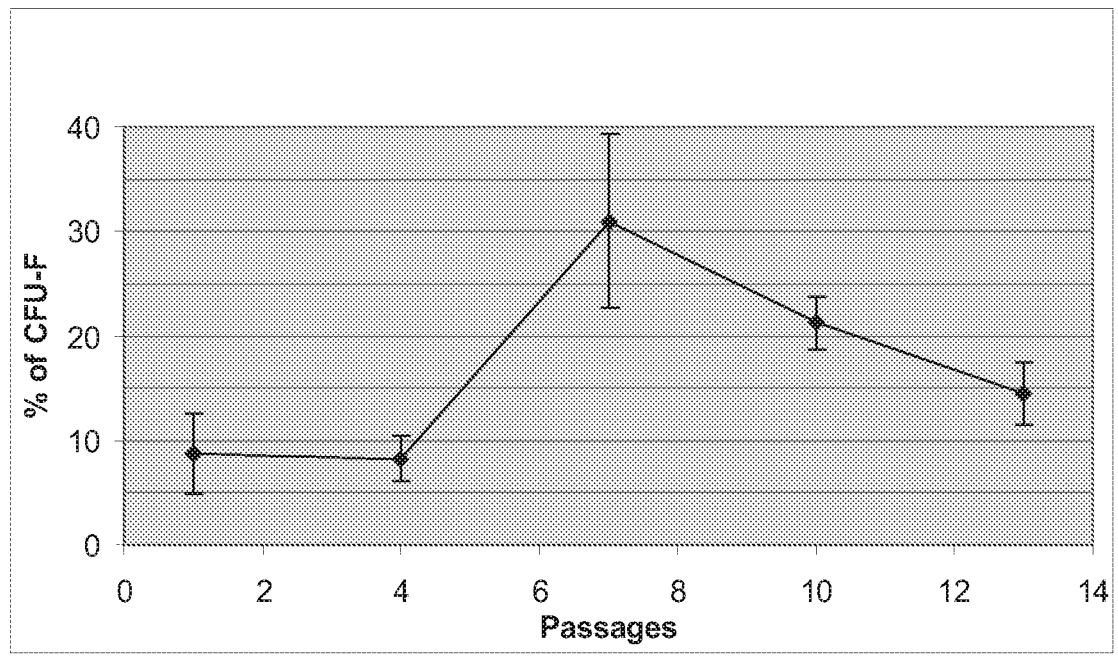
FIG. 4. A graph illustrating the effect of passages on the colony forming efficiency (CFE) of a primary population obtained from the lamina propria of the gingival oral mucosa.
Figure 5A:
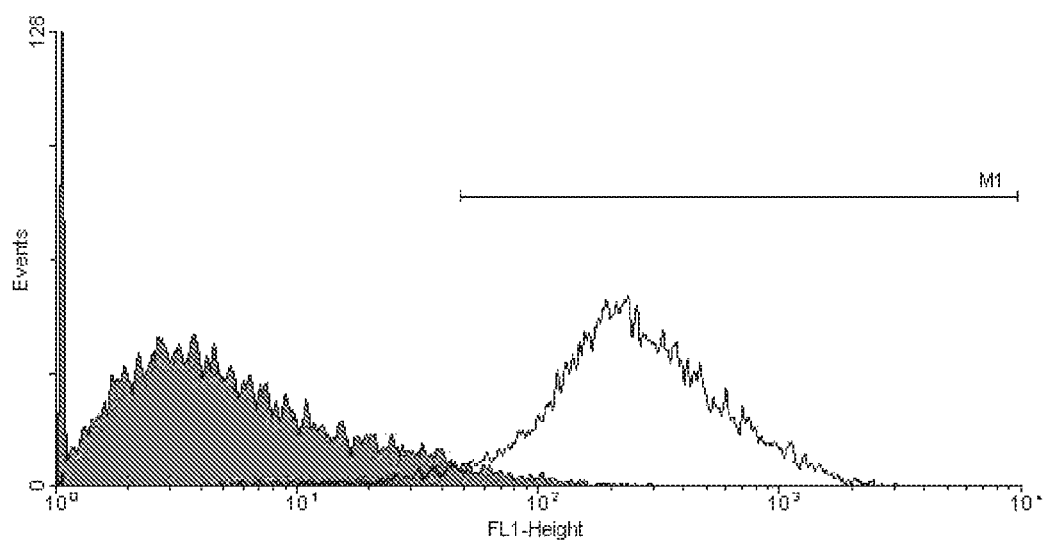
FIGS. 5A-5G. Examples of FACS analysis of mesenchymal multipotent stem cells markers expressed in a whole unsorted population of a culture obtained from the lamina propria of oral mucosa at passage 4. The culture was negative for the hematopoietic cell markers CD45 (FIG. 5C) and CD34 (FIG. 5B), more than 95% of the cells were positive for CD29 (FIG. 5A), CD73 (FIG. 5D), CD90 (FIG. 5E) and CD105 (FIG. 5F), and only 34% of the cells were positive for the marker Stro1 (FIG. 5G).
Figure 5B:
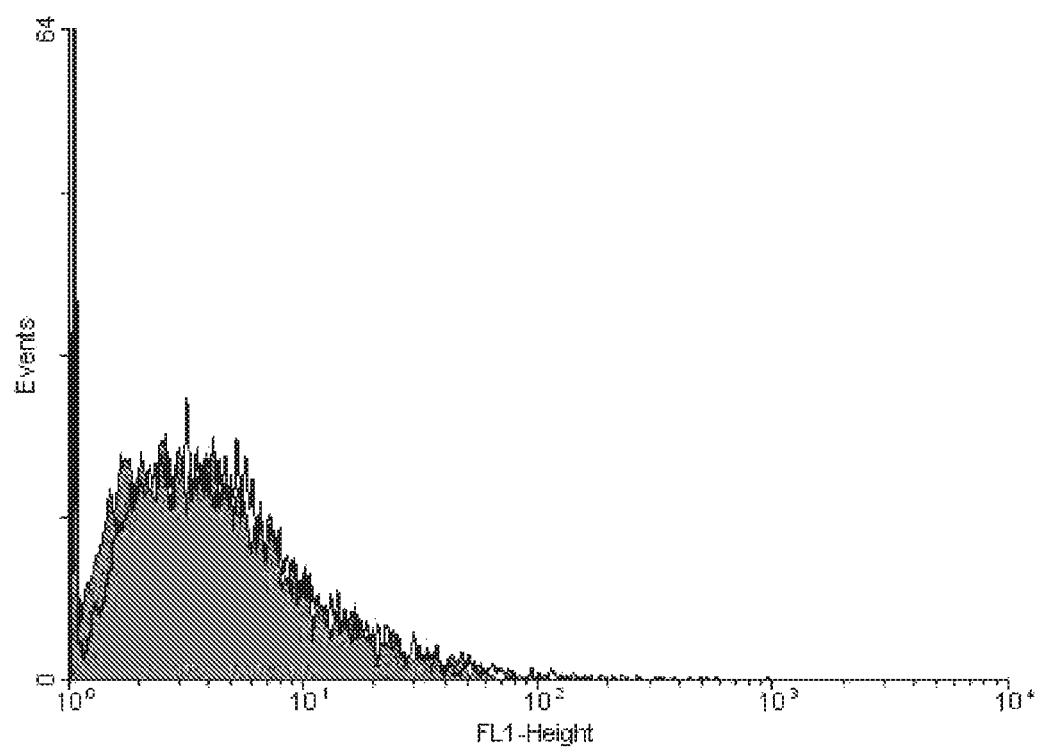
Figure 5C:
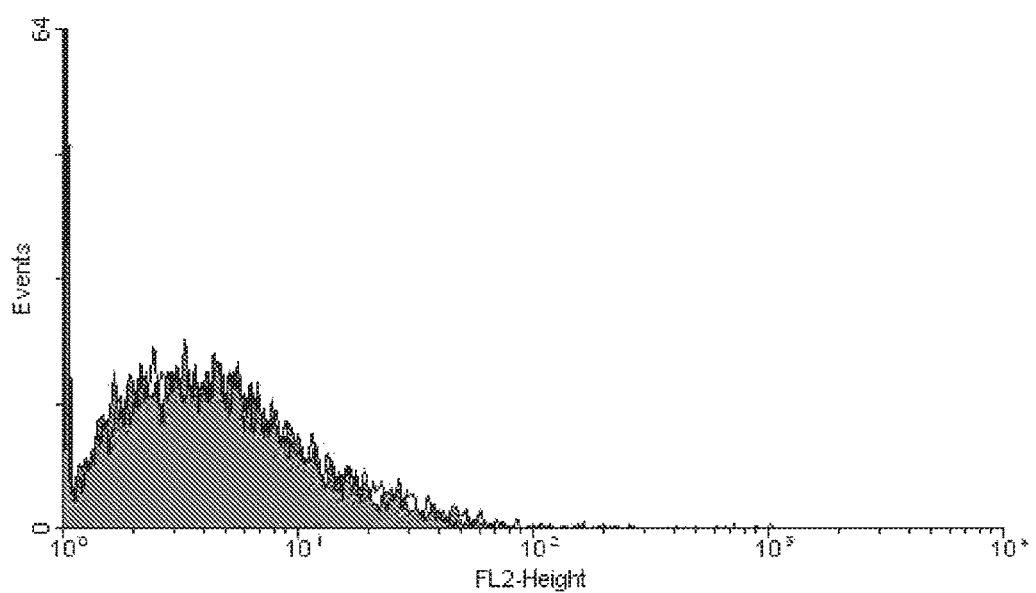
Figure 5D:
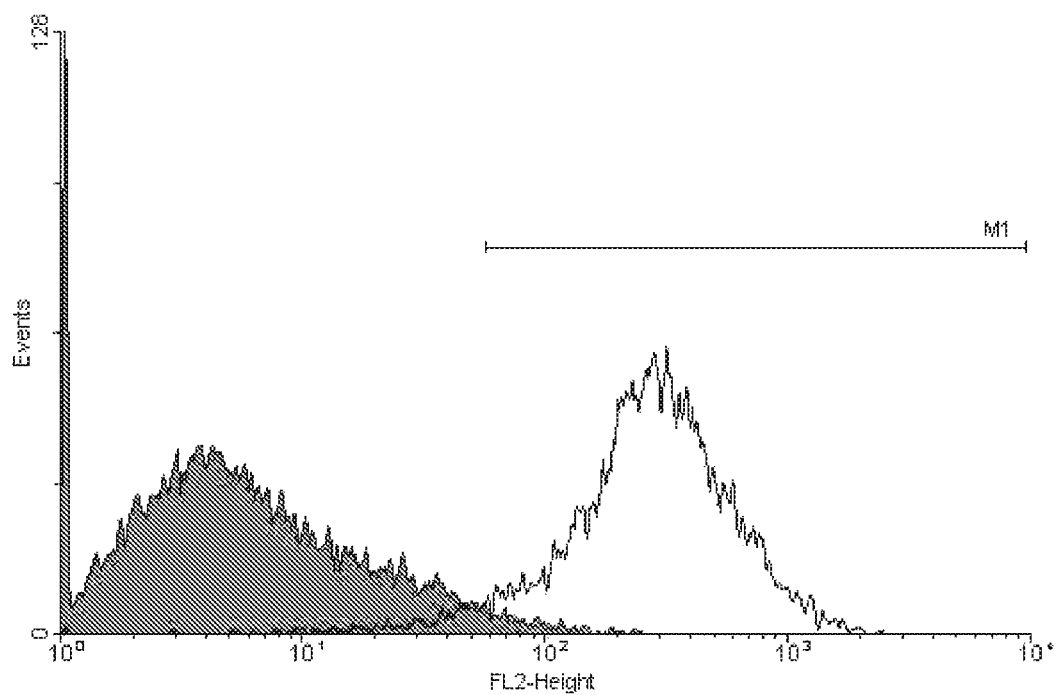
Figure 5E:
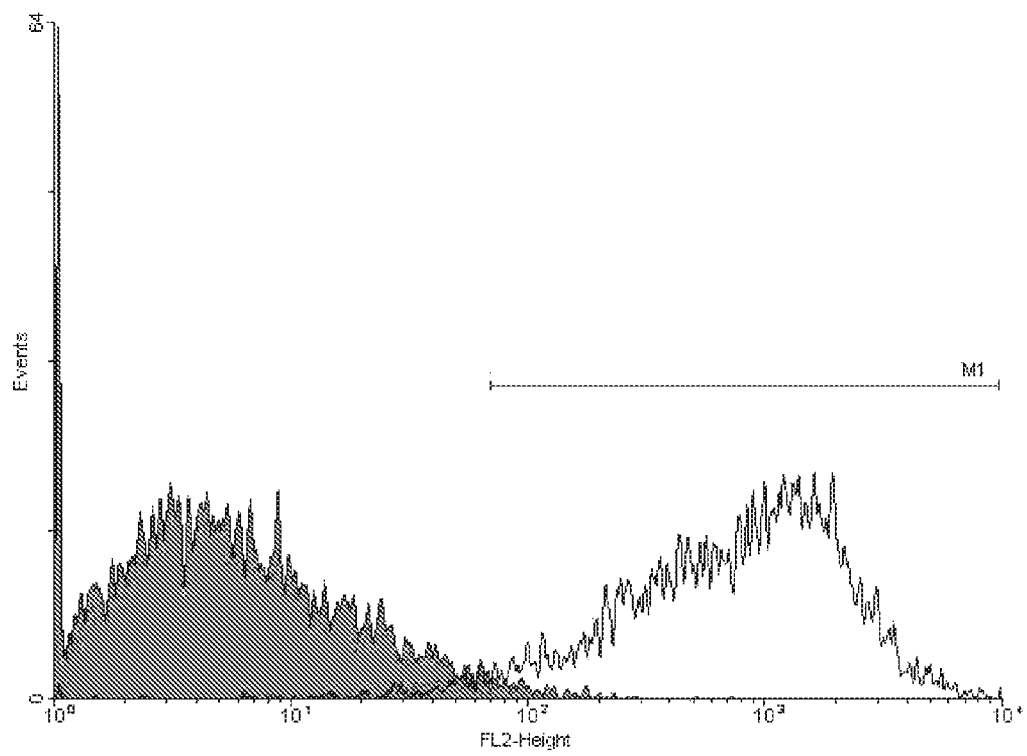
Figure 5F:
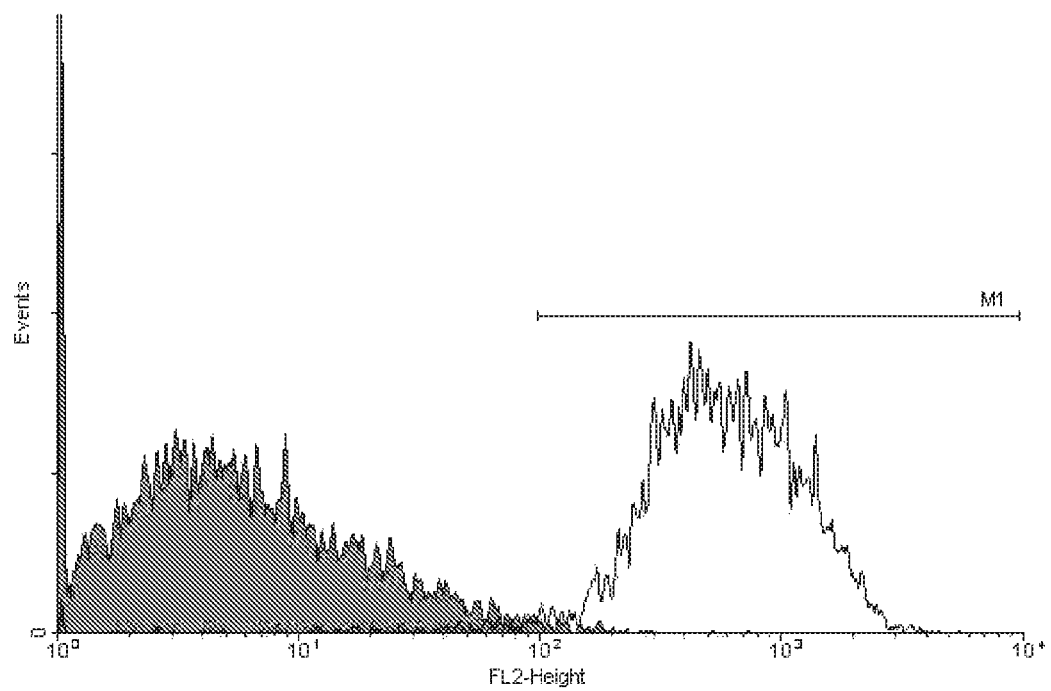
Figure 5G:
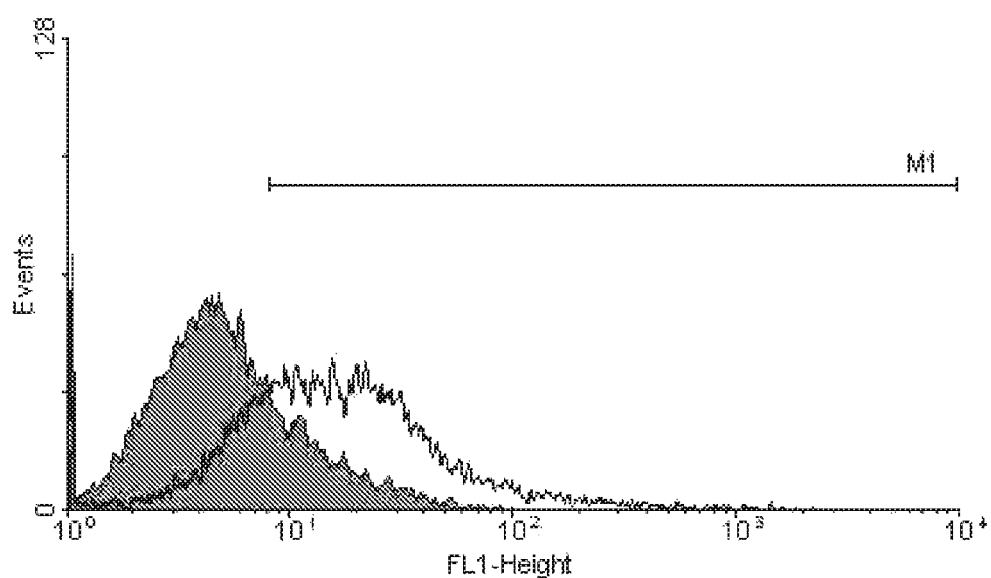

A common method in the art to asses the size of a potential stem cell population in a tissue is to test the number of one cell-derived growing clones that can be derived in vitro from a population of cells obtained from the specific tissue. To assess the general frequency of clonogenic cells in primary oral mucosa cell cultures (OMC), cells were plated at a cloning density of one cell/cm$^2$ and the colony forming unit-fibroblast (CFU-F) was determined. The colony-forming efficiency (CFE) namely the incidence of clonogenic cells capable of forming colonies comprising more than 100 cells, was eight percent. This is a substantially higher value (2-10 folds) compared to previously published values for bone marrow and other connective tissues-derived MSC (Reyes M et al., Blood 96:2615-2625, 2001; D'Ippolito G et al., Rejuvenation Research 9:10-18, 2006). The cells of these colonies are small with low cytoplasm/nucleus ratio as demonstrated in FIG. 3. Interestingly, explants from gingival lamina propria successively continue to produce several successive generations of primary cultures with equivalent growth abilities, suggesting that these explants contain a SC population with high self renewal capacity. $P_1$ cultures and thereafter every $3^{rd}$ passage were plated at a density of 1 cell/cm$^2$ and the number of colonies counted 12 days after plating. The CFE of a population derived from the gingival lamina propria and culture from 13 passages was 8.75% at P1, peaked to 31% at P7 and declined to 14.5% at P13 (FIG. 4). These results show that at least up to 13 passages or 40 population doublings the percentage of cells with self-renewing capacity does not decrease strongly indicating that primary gingival populations are enriched with SC.

Example 2—Determination of OMC Multipotency

Figure 6:
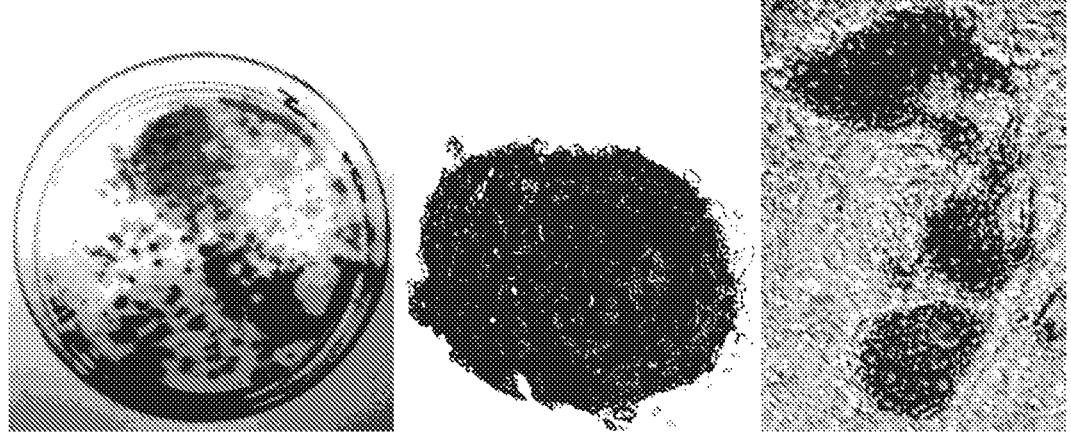
FIG. 6. Differentiation of a whole population of oral mucosa-derived cells (OMC) from the lamina propria of gingival oral mucosa, at P1 into osteogenic (left panel), chondrogenic (middle panel), and adipogenic lineages (right panel). Left panel: mineralized-like tissue formation as reflected by Alizarin red staining; middle panel: chondroblastic differentiation of micromas as evidenced by Alcian blue staining of proteoglycans; right panel: adipogeic differentiation as illustrated by oil red staining of triglyceride droplets.

To determine multiplicity, the size and potency of a whole population to differentiate into various cell lines of various tissues, is checked. The higher the proportion of stem cells in the population the higher the propensity of this whole population to differentiate into a larger number of cell lines. In a such an experiment it was found that in contradistinction to other whole non-bone marrow derived-mesenchymal populations (e.g. dermal fibroblasts), the OMC-primary whole population from the lamina propria of gingival oral mucosa, differentiated into osteoblastic, chondroblastic and adipocytic lineages as demonstrated by: i. Alizarin red staining of mineralized-like tissue (left panel), ii. Alcian blue staining of proteoglycans demonstrating chondroblastic differentiation of micromas (middle panel), and iii, oil red staining of triglyceride droplets representing adypogeic differentiation (FIG. 6, right panel). The results prove that the very vast majority of the whole cell population of OMC cultures consist of multipotent stem cells.

To assess the proportion of multipotent mesenchymal stem cells in the whole OMC populations, cells of the 4-5 passage grown in expansion medium consisting only of low glucose DMEM supplemented with 10% fetal calf serum and in regular cultures flasks or dishes were stained with antibodies for markers known as characteristic for MSC and the number of stained cells was assessed by FACS.

To check whether oral mucosa in general, and the gingiva in particular, is enriched in SC 4-3×2-3×1 mm gingival biopsies were obtained from a group of ten donors aged 18-25 years and a group of ten elder donors aged 60-80 years. Primary cultures were obtained by explanation and expanded in low glucose DMEM+10% FCS. Approximately 20 million cells can be generated from a single biopsy by passage 4 and 1 billion at passage 8. To determine the immunophenotype of the gingival derived populations, cultures at passages 4-8 were assessed for the expression of MSC and ESC cell surface and nuclear markers by flow cytometry, immunofluorescence and RT-PCR. Flow cytometry revealed that more than 95% of the cells in each of the tested population expressed the accepted profile of MSC surface markers—CD29, CD73, CD90, CD106 and CD166 with inter-donor standard deviations ranging between 0.62-3.91 (Table 1 and FIGS. 5A-5G). The results indicate that by utilizing this simple culturing method and without making use of any cumbersome techniques for SC sorting and isolation virtually homogenous cell populations exhibiting the consensus MSC immunophenotype were generated from multiple donors on a reproducible basis.

Further flow cytometry analysis of the population of whole, unsorted population of human gingival-derived stem cells (hGSC) revealed that, cells from this specific donor were negative to CD117, and that about 35% and 30% of the cells co-expressed the cell surface markers Stro1 and CD106 which are mainly detected in MSC located in the paravascular niche in several adult tissues. The perycytes surface marker CD146 was identified only in 16% of the cells indicating that the majority of hGSC do not originated from pericytes-like cell as recently suggested for other adult tissue MSC. hGSC were negative to CD34 and CD45 indicating that they are not of hematopoetic origin. hGSC were negative for HLA-DR but 95% of the cells were positive for HLA-ABC.

hGSC were further assessed to check whether they are positive for cell surface and nuclear markers typical to human ESC. Surprisingly, compared to data reported for MSC derived from adult bone marrow (Reyes, M. et al. Blood 96, 2615-2625, 2001; Gang et al., Blood 109, 1743-1751, 2007) a relatively high percentage of hGSC expressed ESC markers (Table 1). The embryonic cell surface marker SSEA4 and the nuclear proliferation transcription factors Oct4 and Sox2 were immunolocalized in more than 65% of the hGSC (Table 1 and FIGS. 5A-5B) indicating that a major 2. All the cells were negative for the hematopoietic stem cell markers CD34 and 45 (FIGS. 5B and 5C).
3. Only 36% of the cells were positive for Stro1 (FIG. 5G) a marker associated with stem and progenitor cells derived from the stromal bone marrow cells.
4. About 60-74% of the cells were positive for the ESC markers SSEA-4, OCT4 and Sox2.
5. About 25-40% of the cells were positive for the ESC marker Nanog.
6. About 91-96% of the cells were positive for HLA-ABC but the cells were negative for HLA-DR.

TABLE 1

Figure 11A:
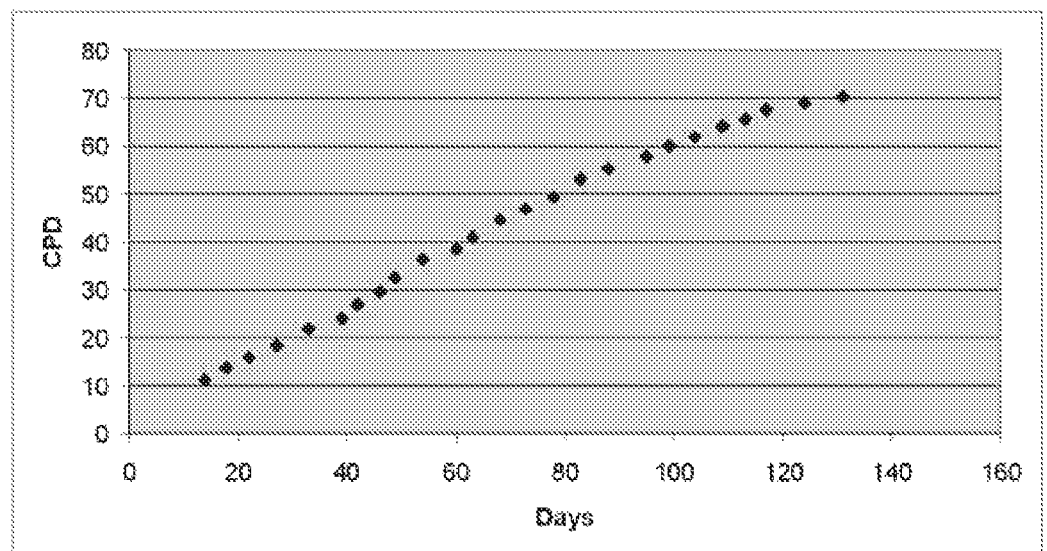
FIGS. 11A and 11B. Representative growth curves depicting the cumulative population doublings (CPD) of a young donor-derived human gingival-derived stem cells (hGSC) population which was expanded for 70 CPD between P1 to P28 (FIG. 11A) and of an elderly donor-derived population expanded for 50 CPD during 27 passages (FIG. 11B).
Figure 11B:
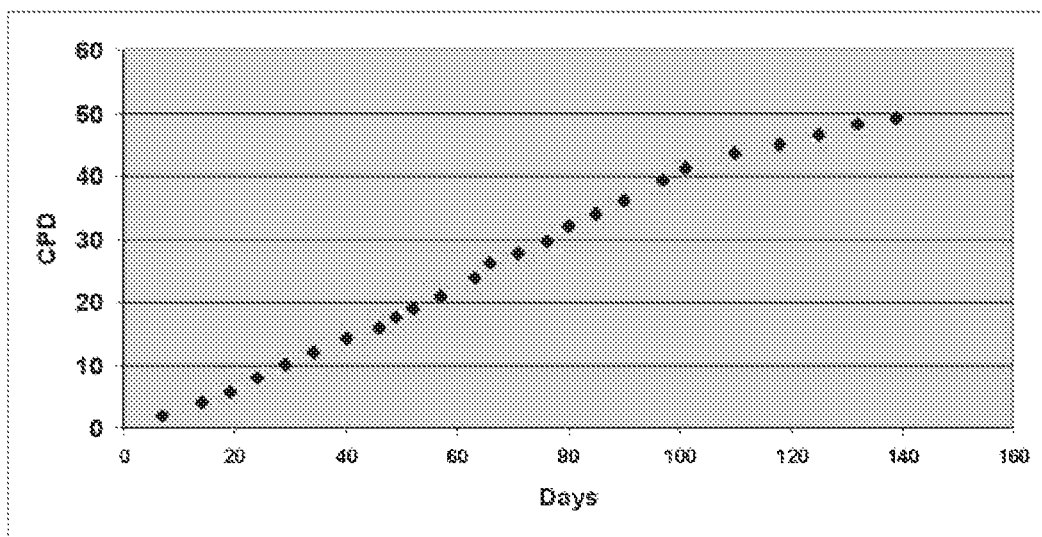

| | Immunophenotype of hGSC | | | | | | |
|---|---|---|---|---|---|---|---|
| | Young Donors | | | Elderly Donors | | Pooled Donors | |
| | Average | SD | p value | Average | SDEV | Average | SD |
| MSC-markers | | | | | | | |
| CD29 | 95.04 | 2.41 | 0.58 | 96.01 | 1.92 | 95.31 | 2.21 |
| CD73 | 96.98 | 2.57 | 0.35 | 94.94 | 4.85 | 95.91 | 3.91 |
| CD90 | 97.87 | 1.13 | 0.34 | 96.16 | 4.65 | 96.68 | 3.56 |
| CD105 | 96.64 | 1.23 | 0.35 | 96.93 | 1.48 | 96.91 | 1.23 |
| CD166 | 98.94 | 0.87 | 0.55 | 98.63 | 0.31 | 98.78 | 0.62 |
| CD106 | 35.37 | 5.558 | 0.13 | 25.61 | 9.53 | 30.49 | 8.91 |
| CD146 | 14.20 | | | 17.10 | 11.26 | 16.92 | 9.20 |
| Stro1 | 35.87 | 9.39 | 0.49 | 30.98 | 11.75 | 34.36 | 9.94 |
| ESC-markers | | | | | | | |
| SSEA4 | 72.96 | 14.01 | 0.64 | 69.32 | 15.12 | 71.50 | 14.04 |
| Tra2-49 | 29.29 | 8.04 | 0.16 | 22.10 | 5.517 | 26.89 | 7.80 |
| Tra2-54 | 23.77 | 9.87 | 0.23 | 17.76 | 3.74 | 21.77 | 8.57 |
| Oct4 | 73.61 | 16.44 | 0.30 | 64.15 | 7.56 | 71.51 | 15.08 |
| Sox2 | 70.48 | 8.07 | 0.07 | 59.74 | 7.911 | 65.45 | 10.06 |
| Nanog | 25.97 | 11.26 | 0.20 | 40.24 | 10.21 | 35.08 | 11.83 |
| Nestin | 68.59 | 11.19 | 0.35 | 77.91 | 14.71 | 73.26 | 13.09 |
| HLA-ABC | 91.75 | 10.25 | 0.63 | 96.48 | 2.09 | 94.12 | 6.63 |
| Negative | | | | | | | |
| CD34 | − | − | | − | − | − | − |
| CD45 | − | − | | − | − | − | − |
| CD117 | − | − | | − | − | − | − |
| SSEA1 | − | − | | − | − | − | − |
| SSEA3 | − | − | | − | − | − | − |
| Tra1-60 | − | − | | − | − | − | − |
| Tra1-81 | − | − | | − | − | − | − |
| HLA-DR | − | − | | − | − | − | − | fraction of hGSC expressed ESC markers constitutively and consequently hGSC may be endowed with pluripotent properties. Semi-quantitative RT-PCR indicates that the expression of Oct4 and Sox were higher than that of Nanog, a finding that is also reflected in the number of Nanog+ hGSC (40%) (FIGS. 11A and 11B, Table 1). Unlike most of ESC lines (Nature Biotech. 25, 803-826, 2007) hGSC were negative for SSEA3, SSEA1, Tra1-60 and Tra1-80. These are markers present in malignancies and their absence in hGSC may reflect safety of these stem cells. Unlike most of ESC lineages hGSC were negative for SSEA3, SSEA1, Tra1-60 and Tra1-80, but 22-26% of these cells expressed Tra2-54 and Tra2-49 similar to some ESC lineages. The expression of Oct4, Sox2, Nanog and the human telomerase reverse transcriptase (hTERT) was demonstrated at the message level.

The results obtained are summarized in Table 1 and FIGS. 5A-5G and show that:
1. More than 95% of the cells in cultures obtained for all the donors were positive for CD29, CD73, CD90, CD105 and CD 166 (FIGS. 5A-5G).

These results demonstrate that the vast majority of the whole unsorted OMC populations generated in culture under regular culture conditions exhibit markers for multipotent mesenchymal stem cells and therefore they are regarded as putative multipotent mesenchymal stem cells. This novel finding has never been reported in prior art for any other whole cell populations generated in culture from tissues other than the oral mucosa without any sorting or any selection procedure.

Example 3—Determination of Cell's Pluripotency

Pluripotency refer to the capacity of a cell population to differentiate to any cell lineage of the adult organism. This property is usually attributed to the embryonic stem cells (ESC). ESC are characterized by a number of surface markers such as: SSEA3, SSEA4, Tra-1-61, Tra-1-81, Tra-2-49, Tra-2-54 and nuclear markers such as POU5F1/Oct-4, Nanog, Sox2 and a few other markers.

The expression of some of these markers at the protein and message level were assessed in whole cultures obtained from several donors. The expression at the protein level was assessed by flow cytometry (FACS) and by indirect immunofluorescence. At the message level the expression was assessed by RT-PCR.

Figure 7A:
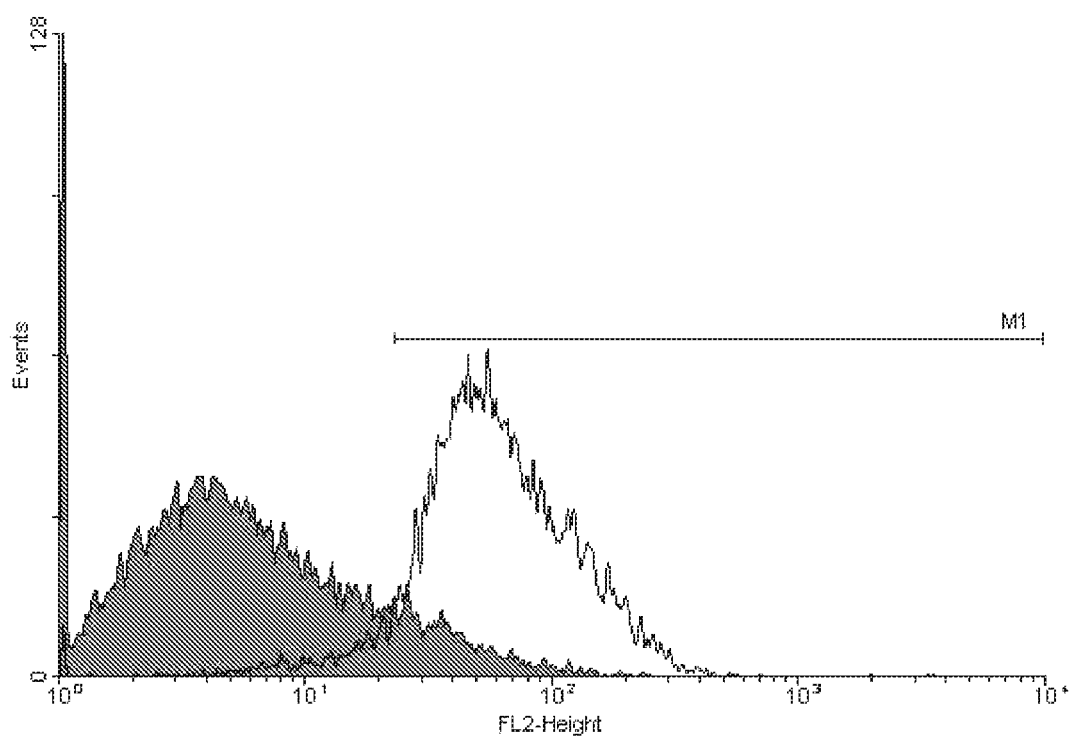
FIGS. 7A and 7B. Examples of FACS analyses of the pluripotent markers Oct4 (FIG. 7A) and SSEA4 (FIG. 7B) markers expressed in a whole unsorted population of a culture obtained from the lamina propria of oral mucosa at passages 4-5.
Figure 7B:
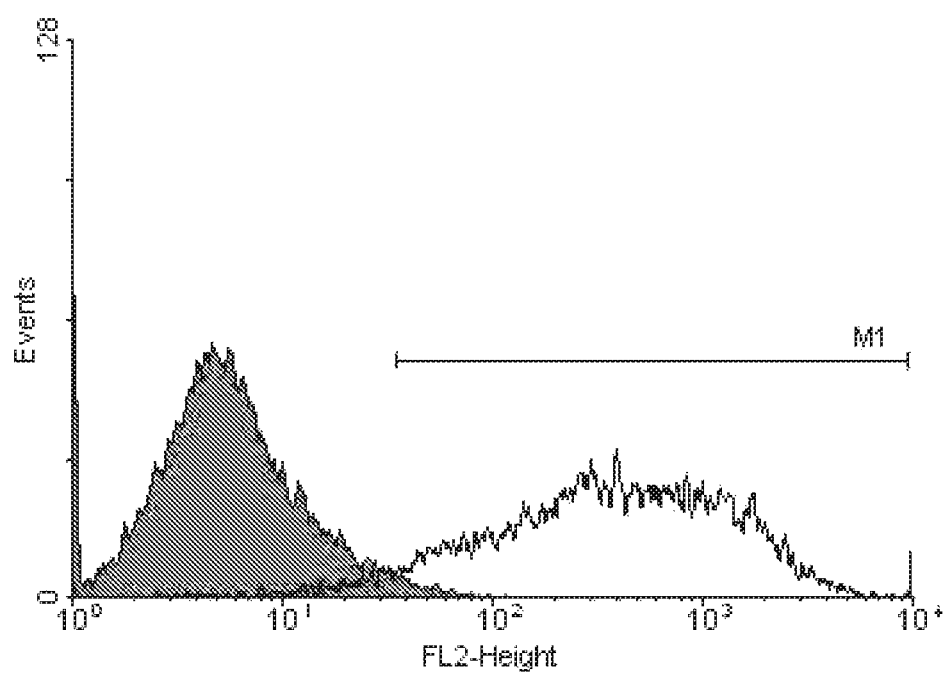
Figure 8:
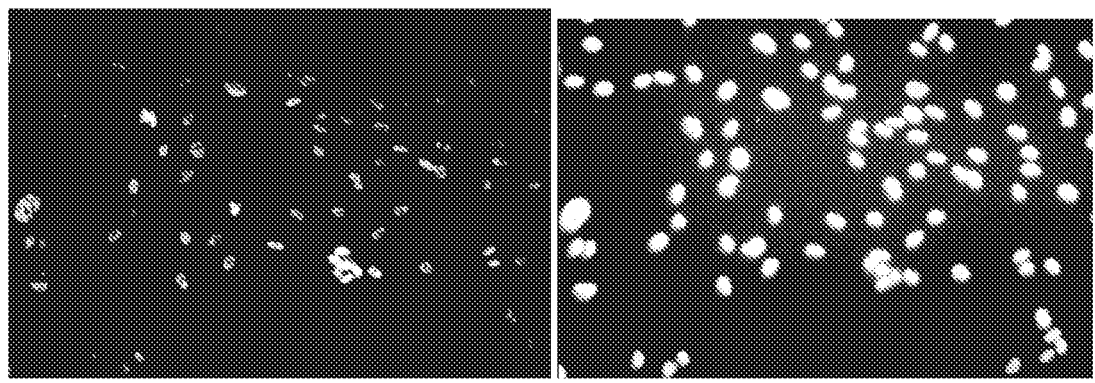
FIG. 8. Example of a passage 2 of whole population from the lamina propria of oral mucosa, stained by immunofluorescence with anti-Sox2 antibodies (left panel) and DAPI for nuclear identification (right panel).
Figure 9:
FIG. 9. Example of RT-PCR analysis of three whole populations each derived from the oral mucosa of a different donor illustrating the expression at the molecular level of the pluripotent markers Sox2. Nanog and Oct4.

The results are summarized in Table 1 and illustrated in FIGS. 7A, 7B-FIG. 9. FIGS. 7A and 7B demonstrate examples of FACS analysis of the pluripotent markers Oct4 (FIG. 7A) and SSEA4 (FIG. 7B) expressed in a whole unsorted population of a culture obtained from the lamina propria of oral mucosa at passages 4-5. FIG. 8 shows example of a passage 2 whole population stained by immunofluorescence with anti-Sox2 antibodies (left panel) and DAPI for nuclear identification (right panel). Comparison between left and right panel indicates that the vast majority of the cells are positive for Sox2 and that the staining is localized to the nucleus. The results indicate that:
  i. more than 60% of the cells express SSEA4, POUF51, Nanog and Sox in cultures obtained from all the tested donors;
  ii. between 10-25% of the cells express Tra-2-54 and Tra-2-49 in cultures obtained from the tested donors;
  ii. Tra-1-61 and Tra-1-81 are expressed only in one donor.

In one specific experiment the expression of part of these markers at the protein level were tested for up to passage 16 which is equivalent to 30 population doublings. The results indicate that the expression pattern virtually remained unchanged.

An additional property of the pluripotent stem cells is their capacity to differentiate into cell lineages the embryonic origin of which is different from that of source tissue. The lamina propria of the oral mucosa is a mesenchymal tissue. To further test the pluripotency of whole (unsorted) OMC cultures, their capacity to differentiate into neuronal cells under appropriate culture conditions was assessed.

Figure 10:
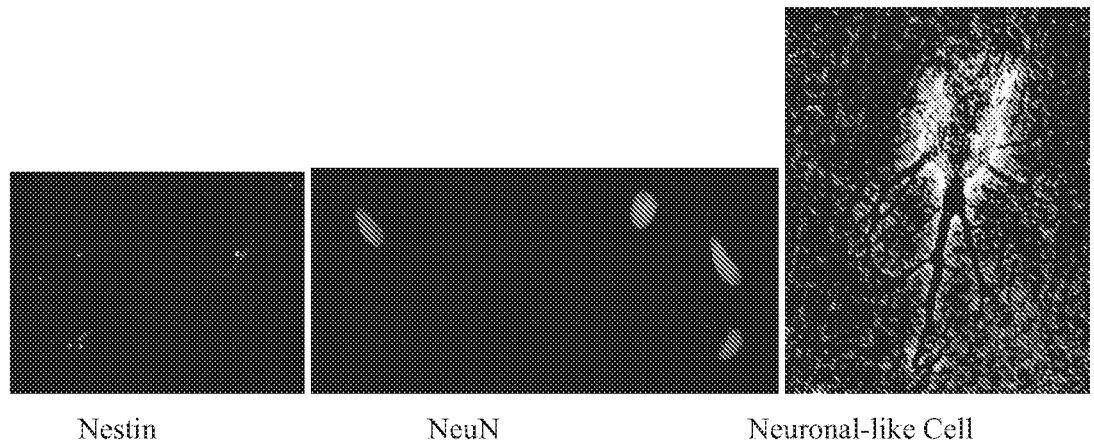
FIG. 10. Example of neural differentiation of a whole unsorted oral mucosa derived population at passage 2. Nestin expression after 48 h of neural induction is illustrated in the left panel. Neuronal nuclear protein (Neu-N) expression during the differentiation stage is depicted in the middle panel. Phase contrast microscopy depicting a neural-like cell with an elongated axon-like process and several dentritic processes at the end of the differentiation stage is shown in the right panel.

First, the expression of nestin, a marker of early progenitors of the nervous system and pancreatic tissue (Zelevzki H. et al., Diabetes 50:521-533, 2001), was determined at the protein and message level in non-stimulated cultures. Immunofluorescence indicates the expression of this marker in the majority of the cells FIG. 8. This finding was confirmed at the message level by RT-PCR FIG. 9. Second, cultures were maintained in neuronal differentiation medium consisting of the components and according to the protocol described above. FIG. 10 illustrated progressive differentiation of the OMC cells to neuronal cells as evidenced at the morphological level by the formation of neuron-like cells and at the cellular level by the step-wise expression of typical neuronal-like markers.

The immunophenotypic analysis of unsorted hGSC populations obtained from multiple donors suggests that these populations are multipotent or pluripotent. To test this presumption whole unsorted hGSC cultures were induced with appropriate differentiation regimens towards specification into cell lineages derived from the three germ layers. Osteogenic, chondrogenic and adipocytic lineages represented mesodermal germ layer.

Nodular mineralized deposits which are characteristic to human osteoblastic cultures derived from bone marrow stromal mesenchymal progenitor cells (Pitaru et al., J Bone Miner. Res. 8, 919-29, 1993) were identified with Alizarin red S staining in 5 weeks old cultures. The early osteogenic differentiation markers Runx2, osterix, collagen type I and alkaline phosphatase were expressed in cultures maintained for 1 week in osteogenic differentiation medium. Differentiation into the adipocytic lineage was shown by demonstrating the expression of the specific adipocytic factors lipoprotein lipase (LPL) and peroxisome proliferators-activated receptor gamma-2 (PPARγ2) in hGSC cultures maintained for 5 weeks in adipocytic differentiation medium and by the positive Oil red O staining of 5-10% of the cells in these cultures. Chondrogenic differentiation was evidenced in micromasses maintained for 5 weeks in chondrogenic medium by positive staining of proteoglycans with alcian blue and by immunolocalization of aggrecan and collagen type II.

Since a major fraction of hGSC expressed an ESC-like immunophenotype and since activin A has been shown to specify ESC to definitive endoderm (DE) it was tested whether activin A can induce unsorted hGSC to differentiate into DE. It was found that 48 hours following activin A induction the vast majority of the cells in unsorted hGSC cultures were positive for the DE markers (D'Amour, K. A. et al., Nature Biotech. 23, 1534-1541, 2005) Sox17 and Foxa2 and 24 hours thereafter the large majority of the cells were positive for CXCR4, demonstrating that hGSC differentiated into a putative DE lineage.

To test the potential of hGSC to differentiate into ectodermal derived-lineages, unsorted hGSC population were subjected to neural differentiation medium for 14 days 48 h after plating. Nestin and the neuron specific 111-tubulin were expressed in the vast majority of the cells in 7 and 14 days old cultures pointing to the development of a profile typical of newly born neurons. MAP2 and Neu-N, two markers of the mature neuronal lineage, were identified at the molecular and protein levels, respectively in 14 days old cultures. These cultures also expressed glial fibrillary acidic protein (GFAP) which is used as a glial marker protein and the early oligodendrocyte marker 04. Notably, a large majority of non-induced control hGSC cultures maintained only in expansion medium were positive for nestin. RT-PCR confirmed nestin expression in these cultures and flow cytometry analysis revealed that 73±13% of hGSC were nestin positive (Table 1). Using double labeling for SSEA4 and nestin we found that 87±3% of the SSEA4 positive cells were also positive for nestin. This was further confirmed at the single cell level. Taken together these finding demonstrate that hGSC express constitutively nestin which is a marker of neural SC and under neuronal induction are capable of differentiating into the three main neural lineages. hGSC grown in neural differentiation medium for 2 weeks, harvested and further expanded in LG-DMEM+2% FCS for 7 passages at a split ratio of 1:3 were positive for nestin and tubulin; this indicated that hGSC have the potential for the establishment of an expandable neuronal progenitor population.

Young donors-derived hGSC were expended between $P_1$ to $P_{28}$ for 70 cumulative population doublings (CPD) (FIGS. 11A and 11B) with an average doubling time of 44.1 hours. This is similar to that reported for fetal SC (Zhang et al. Stem Cells 27, 126-127, 2009). Elderly donor-derived hGSC were expanded between $P_1$ to $P_{27}$ for 50 CPD with an average doubling time of 56 hours which is lower than that reported for MSC derived from adult tissues (Table 1). Considering that the number of population doublings during the development of the primary cultures could not be assessed because of the explanation method used to generate these cultures, the CPD of both young and aged donors-derived hGSC is likely to be beyond the Hayflick limit (Hayflick, L., Moorehead, P. S. Exp. Cell. Res. 25, 585-62, 1961). The average yield of primary cultures obtained from a single biopsy is approximately $5 \times 10^5$ cells. Thus, it is feasible to generate about a trillion hGSC during 3-4 weeks of culture in expansion medium only (passages 4-5).

Primary cultures and whole unsorted hGSC cultures at passages 4-7 cloned by limited dilution exhibited a cloning efficiency of 62±6.3% and 67±10.8%, respectively which are substantially higher than that reported for MSC derived from adult stromal bone marrow cells (Kern et al., Stem Cells 24, 1294-1301, 2006), adipose tissue and umbilical cord, and in the range of fetal bone marrow-derived adherent cells (Zhang et al. Stem Cells 27, 126-127, 2009). The capacity of cloned populations derived by limited dilution from cultures at passages 4-7 to maintain the in vitro functionality of their parent populations was examined by subjecting them to mesodermal, endodermal and neuroectodermal differentiation regimens as described above. Similarly to the parent population, more than 90% of the clones subjected to either osteogenic or chondrogenic regimens formed alizarin red positive mineralized nodules or, alcian blue positive multilayered structures, respectively, and only 50% of the clones subjected to adipocytic regimen formed clusters of oil red O positive cells. Clones inducted with activin A for 72 hour expressed the DE marker CXCR4. Eighty percent of the clonal populations expressed nestin constitutively and differentiated into βIII-tubulin positive cultures upon neural induction.

Example 4. The Effect of Donor Aging on OMC Pluripotency

Oral mucosa biopsies and bone marrow aspirates are obtained from age-matched donors and if possible from the same donor. OMC and BMSC pluripotency are assessed in cultures obtained from the following age groups: 18-25, 35-45 and after 65 years. The following parameters are examined as described above: the OMC size, the frequency of cells expressing primitive markers in the SP and whole populations, their clonogenic capacity, total population doublings, mean doubling time and pluripotency in cultures of P1 and of later passages that are decided according to the data to be obtained in Aim 2. To further test the effect of aging on OMC the cell cycle genes p21 and p27, the cell renewal genes HoxB4 and HoxA9 and the apoptotic genes Bcl-2, Bad and Fas are assessed at the message level by real time-RT-PCR. LP-derived entire populations and age-matched BMSC serve as controls. Biopsies from at least from 4 donors for each age group are assessed.

Since the pattern and rate of gingival wound healing is negligibly affected by age, the effect of donor age on the immunophenotype and functionality of hGSC was tested. By comparing the results obtained from a group of young donors (18-25 years) to those of aged donors (60-80 yrs) it was found that ageing affected only negligibly the immunophenotype of the aged donor as evidenced by the statistically non significant reduction in the number of hGSC positive for the ESC proliferation transcription factors Sox2 and Oct4 (Table 1). However, the number of Nanog$^+$ cells was higher in the elderly group, though the results are not statistically significant. The significance of this apparent trend is unclear. The cloning efficiency was similar for both young and old groups (68±8.39 and 66.23±7.01, respectively). Elderly donors-derived unsorted hGSC cultures differentiated in vitro into derivatives of the 3 germ layers. However, the doubling time of elderly-derived cultures was by 36% higher than that of young-derived ones. These results indicate that at least in vitro, aging does not substantially affect the immunophenotype, clonogenicity and differentiation capacity of hGSC, albeit it reduces their proliferative capacity.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. In a method of treating a tissue disorder or disease, comprising administering to a patient in need thereof multipotent or pluripotent stem cells and providing conditions for differentiation of said cells into cells characterizing said tissue, thereby treating the individual suffering from the tissue disorder or disease, the improvement wherein said pluripotent or multipotent stem cells are pluripotent or multipotent stem cells derived from the lamina propria of the mucosa of the gastrointestinal tract, wherein said stem cells express at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Stro1+.

2. The method according to claim 1, wherein the stem cell derived from the lamina propria of the mucosa of the gastrointestinal tract is derived from an area selected from the group consisting of oral cavity, pharynx, esophagus, stomach and duodenum.

3. The method of claim 2, wherein the stem cell is derived from the lamina propria of the oral mucosa that comprises the gingiva.

4. The method of claim 1, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Stro1+.

5. The method of claim 1, wherein the disorder or disease is selected from the group consisting of hematopoietic disease or disorder, neuronal disease or disorder, cartilage or bone disease or disorder, muscular disease or disorder, ligament disease or disorder, heart disease or disorder, vascular disease or disorder, endothelial disease or disorder, skin disease, liver disease or disorder, pancreatic disease or disorder, gastrointestinal disease or disorder, pulmonary disease or disorder, urogenital disease or disorder, glandular disease or disorder, adrenal disease or disorder, thyroid disease or disorder, and ophthalmologic disease or disorder.

6. In a method of treating an individual suffering from a disorder or disease requiring cell or tissue replacement, comprising introducing isolated somatic multipotent or pluripotent stem cells into a tissue of the individual associated with the disorder, thereby treating the individual suffering from the disorder requiring cell or tissue replacement, the improvement wherein said multipotent or pluripotent stem cells are derived from the lamina propria of the mucosa of the gastrointestinal tract and express at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Stro1+.

7. The method of claim 6, wherein the disorder or disease is selected from the group consisting of hematopoietic disease or disorder, neuronal disease or disorder, cartilage or bone disease or disorder, muscular disease or disorder, ligament disease or disorder, heart disease or disorder, vascular disease or disorder, endothelial disease or disorder, skin disease, liver disease or disorder, pancreatic disease or disorder, gastrointestinal disease or disorder, pulmonary disease or disorder, urogenital disease or disorder, glandular disease or disorder, adrenal disease or disorder, thyroid disease or disorder, and ophthalmologic disease or disorder.

8. In a method of treating an individual suffering from a disorder or disease requiring cell or tissue replacement, comprising introducing a stem cell population into a tissue of the individual associated with the disorder, thereby treating the individual suffering from the disorder requiring cell or tissue replacement, the improvement wherein said stem cell population is an expanded, differentiated, or expanded and differentiated stem cell population obtained by:
   (a) subjecting at least one pluripotent or multipotent stem cell derived from the lamina propria of the mucosa of the gastrointestinal tract, wherein said stem cell expresses at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Strol+, to culturing conditions suitable for inducing cell proliferation, thereby obtaining an expanded stem cell population; or
   (b) subjecting at least one pluripotent or multipotent stem cell derived from the lamina propria of the mucosa of the gastrointestinal tract, wherein said stem cell expresses at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Strol+, to culturing conditions suitable for inducing cell differentiation, thereby obtaining a differentiated stem cell population; or
   (c) subjecting at least one pluripotent or multipotent stem cell derived from the lamina propria of the mucosa of the gastrointestinal tract, wherein said stem cell expresses at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Strol+, to culturing conditions suitable for inducing cell proliferation and differentiation, thereby obtaining an expanded and differentiated stem cell population.

9. The method according to claim 8, wherein the subjecting step of (a), (b) or (c) is the subjecting step of (a).

10. The method according to claim 8, wherein the subjecting step of (a), (b) or (c) is the subjecting step of (b).

11. The method according to claim 8, wherein the subjecting step of (a), (b) or (c) is the subjecting step of (c).

12. The method according to claim 6, wherein the stem cell derived from the lamina propria of the mucosa of the gastrointestinal tract is derived from an area selected from the group consisting of oral cavity, pharynx, esophagus, stomach and duodenum.

13. The method of claim 12, wherein the stem cell is derived from the lamina propria of the oral mucosa comprising the gingiva.

14. The method of claim 6, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Strol+.

15. The method according to claim 8, wherein the stem cell derived from the lamina propria of the mucosa of the gastrointestinal tract is derived from an area selected from the group consisting of oral cavity, pharynx, esophagus, stomach and duodenum.

16. The method of claim 15, wherein the stem cell is derived from the lamina propria of the oral mucosa that comprises the gingiva.

17. The method of claim 8, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Strol+.

18. The method according to claim 9, wherein the stem cell derived from the lamina propria of the mucosa of the gastrointestinal tract is derived from an area selected from the group consisting of oral cavity, pharynx, esophagus, stomach and duodenum.

19. The method of claim 18, wherein the stem cell is derived from the lamina propria of the oral mucosa that comprises the gingiva.

20. The method of claim 9, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Strol+.

21. The method according to claim 10, wherein the stem cell derived from the lamina propria of the mucosa of the gastrointestinal tract is derived from an area selected from the group consisting of oral cavity, pharynx, esophagus, stomach and duodenum.

22. The method of claim 21, wherein the stem cell is derived from the lamina propria of the oral mucosa that comprises the gingiva.

23. The method of claim 10, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Strol+.

24. The method according to claim 11, wherein the stem cell derived from the lamina propria of the mucosa of the gastrointestinal tract is derived from an area selected from the group consisting of oral cavity, pharynx, esophagus, stomach and duodenum.

25. The method of claim 24, wherein the stem cell is derived from the lamina propria of the oral mucosa that comprises the gingiva.

26. The method of claim 11, wherein said stem cell expresses a plurality of the markers selected from the group consisting of Oct-4, Tra-1-61, Tra1-81, SSEA1-4, Rex1, Nanog, Sox2 ABCG2, hTert, Bmi1, CD29, CD44, CD 73, CD90, CD105, CD106, CD117, CD146, CD166 and Strol+.

27. In the method for the treatment of a patient in need thereof by administering pluripotent or multipotent stem cells, the improvement wherein said pluripotent or multipotent stem cells are pluripotent or multipotent stem cells derived from the lamina propria of the mucosa of the gastrointestinal tract, wherein said stem cell expresses at least one stem cell marker selected from the group consisting of Oct-4, Tra-1-61, Tra1-81, Tra-2-49, Tra-2-54, SSEA1-4, Rex1, Nanog, Sox2 ABCG2, hTert, Bmi1, CD29, CD44, CD 73, CD90, CD105, CD106, CD117 CD146, CD166 and Strol+.

* * * * *